(12) United States Patent
Kim

(10) Patent No.: US 12,178,616 B2
(45) Date of Patent: Dec. 31, 2024

(54) METHOD OF DETERMINING BRAIN ACTIVITY AND ELECTRONIC DEVICE PERFORMING THE METHOD

(71) Applicant: Foundation for Research and Business, Seoul National University of Science and Technology, Seoul (KR)

(72) Inventor: Seong Eun Kim, Seoul (KR)

(73) Assignee: Foundation for Research and Business, Seoul National University of Science and Technology, Seoul (KR)

( * ) Notice: Subject to any disclaimer, the term of this patent is extended or adjusted under 35 U.S.C. 154(b) by 105 days.

(21) Appl. No.: 17/974,681

(22) Filed: Oct. 27, 2022

(65) Prior Publication Data

US 2023/0248317 A1    Aug. 10, 2023

(30) Foreign Application Priority Data

Feb. 10, 2022   (KR) .................. 10-2022-0017601
May 16, 2022   (KR) .................. 10-2022-0059495

(51) Int. Cl.
*A61B 5/00*       (2006.01)
*A61B 5/372*      (2021.01)
(Continued)

(52) U.S. Cl.
CPC .......... *A61B 5/7267* (2013.01); *A61B 5/0042* (2013.01); *A61B 5/0075* (2013.01);
(Continued)

(58) Field of Classification Search
CPC ... A61B 5/7267; A61B 5/0042; A61B 5/0075; A61B 5/372; A61B 5/369; G16H 50/20; G16H 40/63; G06F 3/015
See application file for complete search history.

(56) References Cited

U.S. PATENT DOCUMENTS 10,108,902 B1 * 10/2018 Lockett ................ G06F 40/169
11,016,567 B1    5/2021 Nour et al.
(Continued)

FOREIGN PATENT DOCUMENTS

KR    1016809950000    11/2016
KR    20190138051 A    12/2019
(Continued)

OTHER PUBLICATIONS

Kwak et al: FGANet: fNIRS-Guided Attention Network for Hybrid EEG-fNIRS Brain-Computer Interfaces, EMBIEEE Transactions on Neural Systems and Rehabilitation Engineering, vol. 30, 2022.

Primary Examiner — Bo Joseph Peng
(74) Attorney, Agent, or Firm — Blake E. Vande Garde; Avek IP, LLC

(57) ABSTRACT

An electronic device according to an example embodiment includes a processor, and a memory operatively connected to the processor and including instructions executable by the processor, wherein when the instructions are executed, the processor is configured to collect an EEG signal measuring brain activity and an fNIRS signal measuring the brain activity, and output a result of determining a type of the brain activity from a trained neural network model using the EEG signal and the fNIRS signal, and the neural network model may be trained to, extract an EEG feature from the EEG signal, extract an fNIRS feature from the fNIRS signal, extract a fusion feature based on the EEG signal and the fNIRS signal, and output the result of determining the type of the brain activity based on the EEG feature and the fusion feature.

14 Claims, 16 Drawing Sheets

(51) Int. Cl.
*G16H 50/20* (2018.01)
*G06F 3/01* (2006.01)
(52) U.S. Cl.
CPC ............ *A61B 5/372* (2021.01); *G16H 50/20* (2018.01); *G06F 3/015* (2013.01)

(56) References Cited

U.S. PATENT DOCUMENTS

| | | | |
|---|---|---|---|
| 2018/0232606 A1* | 8/2018 | Park | G06N 3/04 |
| 2018/0307112 A1 | 10/2018 | Park et al. | |
| 2018/0349477 A1* | 12/2018 | Jaech | G06F 16/9535 |
| 2019/0019037 A1* | 1/2019 | Kadav | G06F 18/217 |
| 2021/0174093 A1* | 6/2021 | Li | G06N 3/045 |
| 2021/0390313 A1* | 12/2021 | Gubbi Lakshminarasimha | G06V 10/82 |
| 2023/0153608 A1* | 5/2023 | Zhou | G06N 3/08 |
| | | | 706/25 |

FOREIGN PATENT DOCUMENTS

| | | |
|---|---|---|
| KR | 20200132355 A | 11/2020 |
| KR | 1021799830000 | 11/2020 |

* cited by examiner

METHOD OF DETERMINING BRAIN ACTIVITY AND ELECTRONIC DEVICE PERFORMING THE METHOD

CROSS-REFERENCE TO RELATED APPLICATION

This application claims the benefit of Korean Patent Application No. 10-2022-0017601 filed on Feb. 10, 2022, and Korean Patent Application No. 10-2022-0059495 filed on May 16, 2022 at the Korean Intellectual Property Office, the entire disclosures of which are incorporated herein by reference for all purposes.

BACKGROUND

1. Field of the Invention

One or more example embodiments relate to a method of determining brain activity, and an electronic device for performing the method.

2. Description of the Related Art

A brain-computer interface (BCI) provides a direct interface between neural activity including user intent and control signals for external devices.

A BCI system may enable an individual to operate an assistive device such as a robotic arm, a wheelchair, and the like.

The BCI system may be based on an electroencephalography (EEG) and functional near-infrared spectroscopy (fNIRS). An EEG may measure macro-temporal dynamics of neuroelectric activity through multi-channel electrodes but may be vulnerable to human motion or noise. An fNIRS technique, which relates to optical spectroscopic measurement in which hemodynamic fluctuations caused by brain activity are measured using a light injection source and detector, may be resistant to human motion and noise, but may provide low temporal resolution and hemodynamic response may be delayed.

SUMMARY

Example embodiments may provide a method, and an electronic device for performing the method of determining brain activity capable of improving performance compared to an EEG or fNIRS standalone BCI system by combining the advantages of an EEG signal and an fNIRS signal.

Example embodiments may provide a data processing method, and a neural network model training method using the data processing method capable of improving performance compared to an EEG or fNIRS standalone BCI system by combining the advantages of an EEG signal and an fNIRS signal.

According to an aspect, an electronic device is provided, including a processor, and a memory operatively connected to the processor and including instructions executable by the processor, wherein when the instructions are executed, the processor is configured to collect an EEG signal measuring brain activity and an fNIRS signal measuring the brain activity, and output a result of determining a type of the brain activity from a trained neural network model using the EEG signal and the fNIRS signal, and the neural network model may be trained to, extract an EEG feature from the EEG signal using an EEG branch including a plurality of sequentially connected convolutional layers, extract an fNIRS feature from the fNIRS signal using an fNIRS branch including a plurality of sequentially connected convolutional layers, extract a fusion feature based on the EEG signal and the fNIRS signal using a fusion branch including a plurality of sequentially connected convolutional layers and an fNIRS-guided attention (FGA) layer, and output the result of determining the type of the brain activity based on the EEG feature and the fusion feature.

The FGA layer may output a fusion feature of a next step using the input EEG feature, a fusion feature of a previous step, and the fNIRS feature, and the fusion feature of the previous step may be output from a convolutional layer of a front-end of the FGA layer, and the fusion feature of the next step may be input to a convolutional layer or a temporal attention pooling (TAP) layer of a back-end of the FGA layer.

The FGA layer may output an FGA map from the fNIRS feature by applying a weight to a time segment related to the brain activity using the TAP layer included in the FGA layer, and output the fusion feature of the next step by processing the EEG feature and the fusion feature of the previous step according to the FGA map and a residual parameter.

The TAP layer may compress a feature having input height, width, time, and channel dimensions on a time axis of the feature.

The neural network model may output a first result based on the EEG feature, output a second result based on the fusion feature, and output the result by applying a weight assigned to each of the first result and the second result.

According to another aspect, a method of determining brain activity is provided, including collecting an EEG signal measuring brain activity and an fNIRS signal measuring the brain activity, and outputting a result of determining a type of the brain activity from a trained neural network model using the EEG signal and the fNIRS signal, and wherein the neural network model is trained to, extract an EEG feature from the EEG signal using an EEG branch including a plurality of sequentially connected convolutional layers, extract an fNIRS feature from the fNIRS signal using an fNIRS branch including a plurality of sequentially connected convolutional layers, extract a fusion feature based on the EEG signal and the fNIRS signal using a fusion branch including a plurality of sequentially connected convolutional layers and an FGA layer, and output the result of determining the type of the brain activity based on the EEG feature and the fusion feature.

The FGA layer may output a fusion feature of a next step using the input EEG feature, a fusion feature of a previous step, and the fNIRS feature, and the fusion feature of the previous step may be output from a convolutional layer of a front-end of the FGA layer, and the fusion feature of the next step may be input to a convolutional layer or a TAP layer of a back-end of the FGA layer.

The FGA layer may output an FGA map from the fNIRS feature by applying a weight to a time segment related to the brain activity using the TAP layer included in the FGA layer, and output the fusion feature of the next step by processing the EEG feature and the fusion feature of the previous step according to the FGA map and a residual parameter.

According to another aspect, a training method of a neural network model is provided, including collecting an EEG signal measuring brain activity and an fNIRS signal measuring the brain activity of a motor imagery (MI) data set and a mental arithmetic (MA) data set, extracting an EEG feature from the EEG signal using an EEG branch including a plurality of sequentially connected convolutional layers, extracting an fNIRS feature from the fNIRS signal using an fNIRS branch including a plurality of sequentially connected convolutional layers, extracting a fusion feature based on the EEG signal and the fNIRS signal using a fusion branch including a plurality of sequentially connected convolutional layers and an FGA layer, outputting a result of determining a type of the brain activity based on the EEG feature and the fusion feature, calculating a loss based on the result and a labeling of the EEG signal and the fNIRS signal, and training a neural network model using the loss.

The extracting of the fusion feature may include outputting a fusion feature of a next step by inputting the EEG feature, a fusion feature of a previous step, and the fNIRS feature, and the fusion feature of the previous step may be output from a convolutional layer of a front-end of the FGA layer, and the fusion feature of the next step may be input to a convolutional layer or a TAP layer of a back-end of the FGA layer.

The FGA layer may output an FGA map from the fNIRS feature by applying a weight to a time segment related to the brain activity using the TAP layer included in the FGA layer, and output the fusion feature of the next step by processing the EEG feature and the fusion feature of the previous step according to the FGA map and a residual parameter.

The TAP layer may compress a feature having input height, width, time, and channel dimensions on a time axis of the feature.

The outputting of the result of the determining may include outputting a first determination result based on the EEG feature, outputting a second determination result based on the fusion feature, and applying a weight assigned to each of the first determination result and the second determination result.

The calculating of the loss may include calculating a classification loss based on the result and the labeling, calculating an fNIRS classification loss (cross entropy loss) of the fNIRS branch based on the fNIRS feature, and calculating a correlation coefficient loss of the EEG signal and the fNIRS signal.

According to another aspect, a data processing method is provided, including receiving a first feature, a second feature of a previous step, and a third feature, outputting an attention map representing a spatial weight matrix from the third feature using a TAP layer, and outputting a second feature of a next step by processing the first feature and the second step of the previous step according to the attention map and a residual parameter.

Additional aspects of example embodiments will be set forth in part in the description which follows and, in part, will be apparent from the description, or may be learned by practice of the disclosure.

According to example embodiments, a method of determining brain activity and an electronic device performing the method may have improved performance compared to an EEG or fNIRS stand-alone BCI system as a result of an EEG signal and an fNIRS signal being combined.

According to example embodiments, spatial alignment of EEG and fNIRS signals may be performed by converting 1D EEG and fNIRS signals into 3D EEG and fNIRS tensors according to a spatial alignment method.

According to example embodiments, an initial fusion method called an fNIRS-guided attention layer may be provided, wherein fNIRS may guide a region important for brain decoding and apply spatial attention to EEG features.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
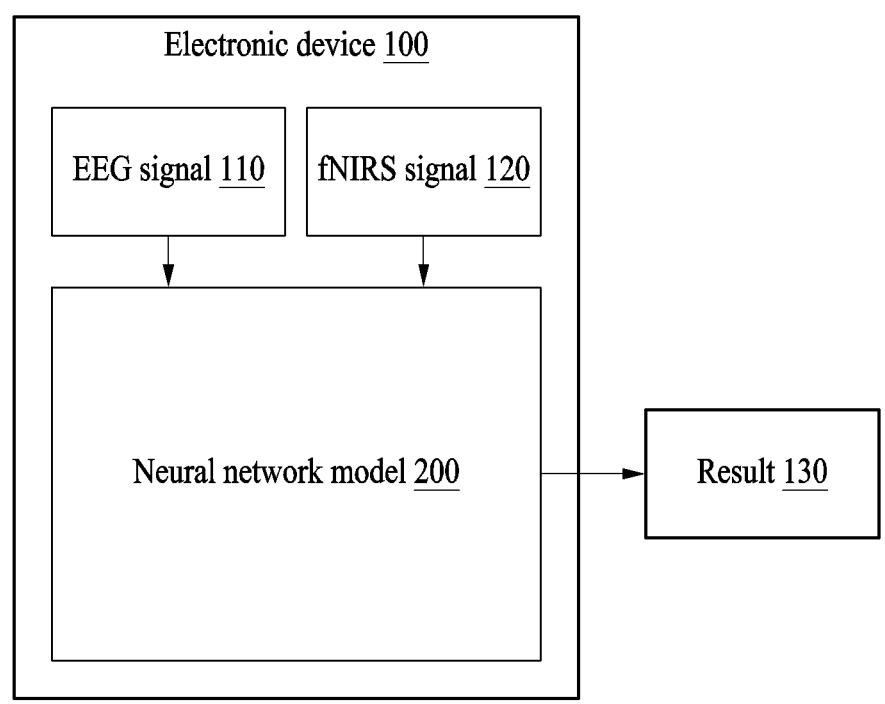
FIG. 1 is a diagram illustrating an operation of outputting a result of determining brain activity of an electronic device according to an example embodiment.

Hereinafter, example embodiments will be described in detail with reference to the accompanying drawings. However, various alterations and modifications may be made to the example embodiments. Here, the example embodiments are not meant to be limited by the descriptions of the present disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the examples with reference to the accompanying drawings, like reference numerals refer to like constituent elements and a repeated description related thereto will be omitted. In the description of the example embodiments, a detailed description of well-known related structures or functions will be omitted when it is deemed that such description will cause ambiguous interpretation of the present disclosure.

FIG. 1 is a diagram illustrating an operation of outputting a result 130 of determining brain activity of an electronic device 100 according to an example embodiment.

Referring to FIG. 1, a processor (not shown) of the electronic device 100 according to various example embodiments may collect an EEG signal 110 and an fNIRS signal 120. For example, the EEG signal 110 and the fNIRS signal 120 may be signals simultaneously collected from a measurement target. For example, the EEG signal 110 may be a signal obtained by electrically measuring brain activity of the measurement target, and the fNIRS signal 120 may be a signal obtained by optically measuring brain activity of the measurement target.

In an example embodiment, the EEG signal 110 collected by the processor of the electronic device 100 may be a three-dimensional (3D) EEG image or tensor, and the fNIRS signal 120 collected by the processor of the electronic device 100 may be a 3D fNIRS image or tensor.

As another example, the processor of the electronic device 100 may collect, a one-dimensional (1D) EEG signal 110 and a 1D fNIRS signal 120, and process the collected 1D EEG signal 110 and 1D fNIRS signal 120 to generate a 3D EEG image or tensor, and a 3D fNIRS image or tensor.

For example, the EEG signal 110 and the fNIRS signal 120 collected by the processor may include spatial information and time information. For example, the EEG signal 110 and the fNIRS signal 120 may have height and width dimensions, and a measured time dimension, since a position of a 3D electrode or a position of an fNIRS channel on the scalp of the measurement target of the EEG signal 110 and the fNIRS signal 120, respectively, may be projected as a two-dimensional (2D) image. The EEG signal 110 and the fNIRS signal 120 may be measured simultaneously, and may be spatially aligned.

In an example embodiment, the processor of the electronic device 100 may output the result 130 of determining a type of brain activity from a trained neural network model 200 using the EEG signal 110 and the fNIRS signal 120.

In an example embodiment, the neural network model 200 may be trained using a motor imagery (MI) data set or a mental arithmetic (MA) data set as training data. For example, the MA data set may be labeled as a baseline state or an MA task, and the MI data set may be labeled as a left-hand MI task or a right-hand MI task.

For example, the MI task may be an operation in which the measurement target imagines opening and closing their left hand or right hand. For example, the MA task may be an operation in which the measurement target performs subtraction or addition of three-digit numbers.

For example, when the neural network model 200 is trained using the MI data set, the electronic device 100 may determine whether brain activity measured by the EEG signal 110 and the fNIRS signal 120 relates to a left-hand MI task or a right-hand MI task using the trained neural network model 200.

For example, when the neural network model 200 is trained using the MA data set, the electronic device 100 may determine whether brain activity measured by the EEG signal 110 and the fNIRS signal 120 relates to a baseline state or an MA task using the trained neural network model 200.

In an example embodiment, the neural network model 200 may be trained to determine a type of brain activity corresponding to an input EEG signal 110 and an input fNIRS signal 120. For example, the neural network model 200 may include an EEG branch, a fusion branch, or an fNIRS branch.

In an example embodiment, the EEG branch may include a plurality of sequentially connected convolutional layers, and may extract an EEG feature from the EEG signal 110. In an example embodiment, the fusion branch may include a plurality of sequentially connected convolutional layers, and may extract a fusion feature from the EEG signal 110 and the fNIRS signal 120. In an example embodiment, the fNIRS branch may include a plurality of sequentially connected convolutional layers, and may extract an fNIRS feature from the fNIRS signal 120.

In an example embodiment, the neural network model 200 of the electronic device 100 may output the result 130 based on a fusion feature and an EEG feature. The neural network model 200 according to an example embodiment may improve accuracy of the determination result 130 compared to the standalone BCI system using an EEG or fNIRS, respectively, by outputting the determination result 130 from the EEG signal 110 and the fNIRS signal 120.

For example, the neural network model 200 may process an EEG feature extracted using the EEG signal 110 by using a fully connected (FC) layer and a softmax layer, to output a first result. For example, the neural network model 200 may process a fusion feature extracted using the EEG signal 110 and the fNIRS signal 120 by using a softmax layer, to output a second result. In an example embodiment, the neural network model 200 may output the result 130 using a weighted sum of the first result and the second result.

The neural network model 200 of the electronic device 100 according to an example embodiment may prevent performance degradation due to mismatch between temporal resolution and recording position in a hybrid BCI system using the EEG signal 110 and the fNIRS signal 120, by outputting the determination result 130 based on a fusion feature.

The EEG signal 110 may be measured via a multi-channel electrode, and macro-temporal dynamics of a neuroelectric activity may be measured via the EEG signal 110. In particular, the EEG signal 110 may have a high temporal resolution and response to a stimulus may be fast. However, the EEG signal 110 may be vulnerable to a motion of the measurement target or electrical noise.

The fNIRS signal 120 may be measured by an optical spectroscopic measurement method using a light injection source and a detector. For example, the fNIRS signal 120 may be measured via a decrease in oxygenated hemoglobin (HbO) and an increase in deoxygenated hemoglobin (HbR) according to neural activity. The fNIRS signal 120 may be resistant to motion of the measurement target or electrical noise, but may have low temporal resolution, and hemodynamic response may be delayed causing a time delay between measurement and actual brain activity.

In an example embodiment, the electronic device 100 according to an example embodiment may convert the 1D EEG signal 110 and the 1D fNIRS signal 120 into the 3D EEG signal 110 and the 3D fNIRS signal 120 to spatially align the EEG signal 110 and the fNIRS signal 120 at the same time point. For example, the 3D EEG signal 110 and the 3D fNIRS signal 120 may be considered as equivalent to a 3D EEG tensor and a 3D fNIRS tensor, respectively. The neural network model 200 of the electronic device 100 may include an fNIRS-guided attention (FGA) layer. The electronic device 100 may identify a spatially significant region in the fNIRS signal 120 using the FGA layer, and extract a feature from the EEG signal 110 and the fNIRS signal 120 based on neurovascular coupling. The electronic device 100 may extract a detailed neural pattern from the EEG signal 110 using the FGA layer. The electronic device 100 may reduce performance degradation due to a response delay of the fNIRS signal 120 by outputting the determination result 130 using a weighted sum of an EEG feature extracted from the EEG signal 110 and a fusion feature extracted via the FGA layer.

The feature through which performance degradation due to a response delay of the fNIRS signal 120 is reduced by outputting the determination result 130 using the EEG signal 110 and the fNIRS signal 120 of the electronic device 100 may be substantially equally applied to a training apparatus for training the neural network model 200 to be described below. For example, the neural network model 200 trained by the training apparatus may have a feature through which performance degradation due to a response delay of the fNIRS signal 120 is reduced.

According to an example embodiment, the processor may execute software to control at least one other component (e.g., the neural network model 200) of the electronic device 100 connected to the processor, and perform various data processing tasks or computations. According to an example embodiment, as at least a part of data processing or computation, the processor may store a command or data received from the other component (e.g., a memory or the neural network model 200) in a volatile memory, process the command or the data stored in the volatile memory, and store the result 130 data in a non-volatile memory.

In an example embodiment, the memory (not shown) of the electronic device 100 may store a variety of data (e.g., the EEG signal 110, the fNIRS signal 120, and the determination result 130) used by at least one component (e.g., the neural network model 200) of the electronic device 100. The variety of data may include, for example, the neural network model 200 and input data or output data for a command related thereto. The memory may include, for example, a volatile memory or a non-volatile memory.

Figure 2:
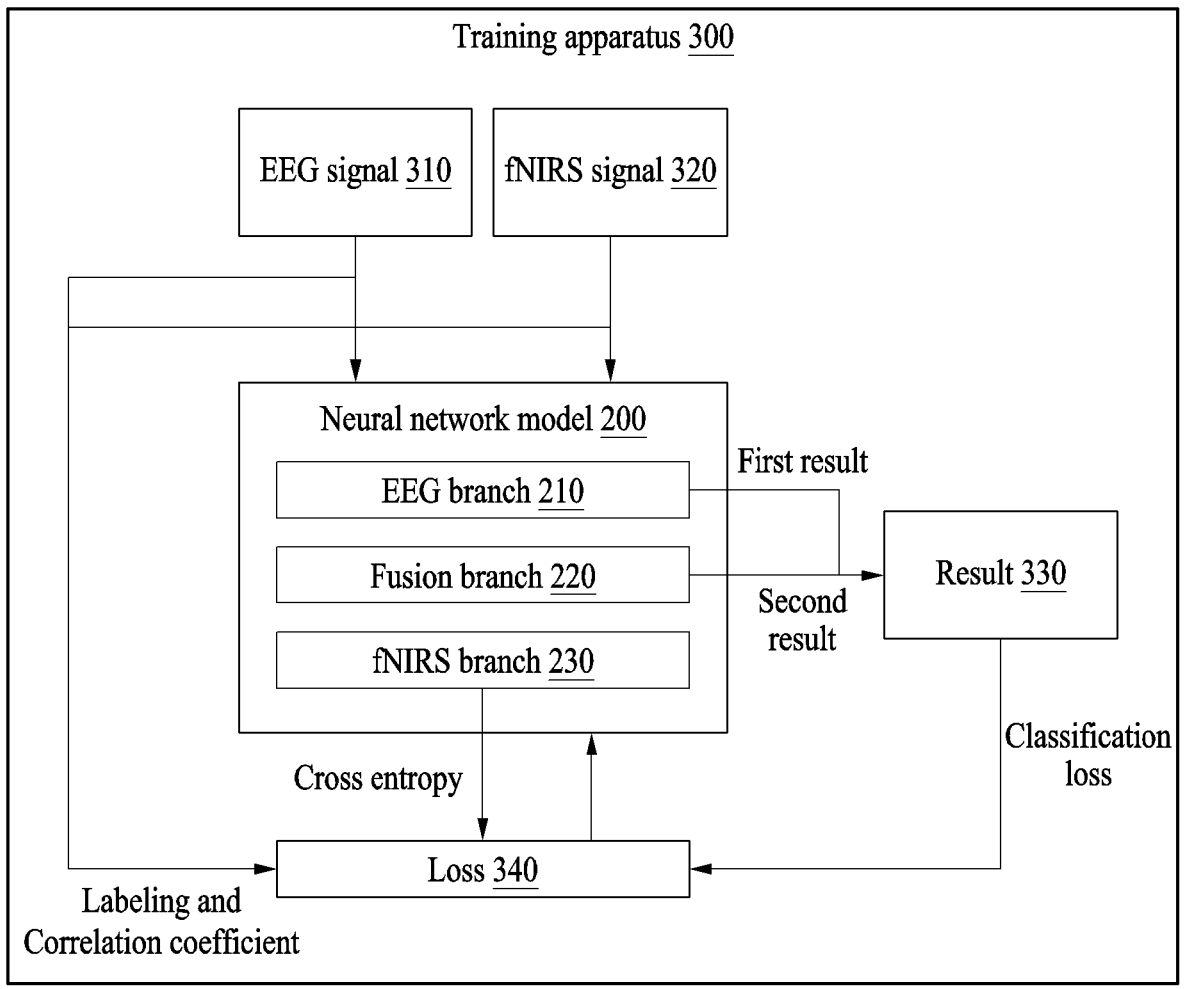
FIG. 2 is a diagram illustrating an operation of training a neural network model of a training apparatus according to an example embodiment.

FIG. 2 is a diagram illustrating an operation of training a neural network model 200 of a training apparatus 300 according to an example embodiment.

Referring to FIG. 2, the training apparatus 300 according to various example embodiments may train the neural network model 200 to output a determination result 330. In an example embodiment, the electronic device 100 of FIG. 1 may use the neural network model 200 trained by the training apparatus 300 of FIG. 2, and the neural network model 200 of FIG. 1 may be the neural network model 200 trained by the training apparatus 300 of FIG. 2.

Referring to FIG. 2, the training apparatus 300 according to various example embodiments may collect an EEG signal 310 and an fNIRS signal 320. For example, the EEG signal 310 and the fNIRS signal 320 collected by the training apparatus 300 may be a 3D EEG image or tensor, and a 3D fNIRS image or tensor, respectively.

As another example, a processor (not shown) of the training apparatus 300 may collect a 1D EEG signal 310 and a 1D fNIRS signal 320, and process the collected 1D EEG signal 310 and 1D fNIRS signal 320 to generate a 3D EEG image or tensor, and a 3D fNIRS image or tensor.

Figure 8:
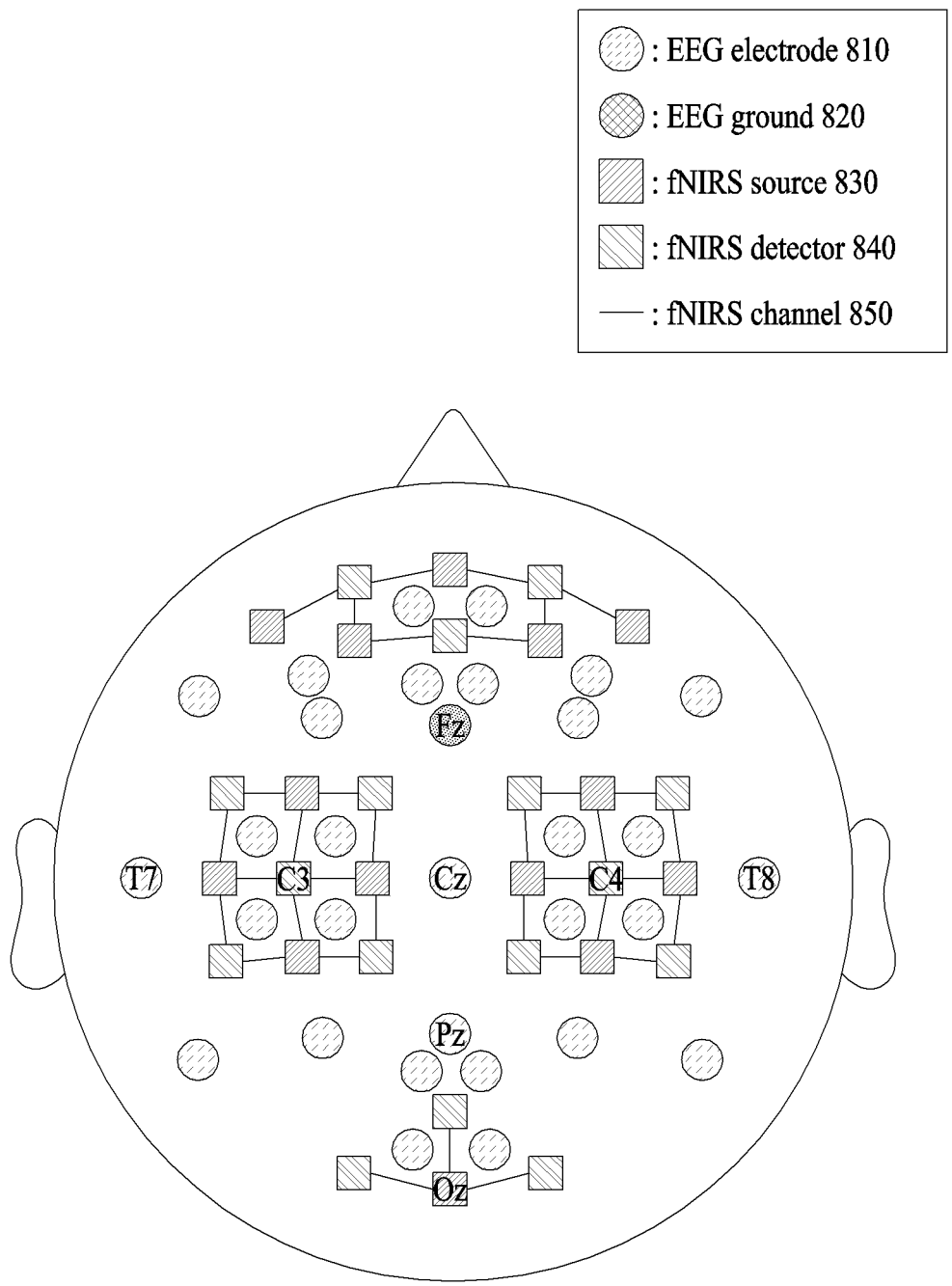
FIG. 8 is a diagram illustrating an EEG electrode, an fNIRS source, and a detector according to an example embodiment.
Figure 9:
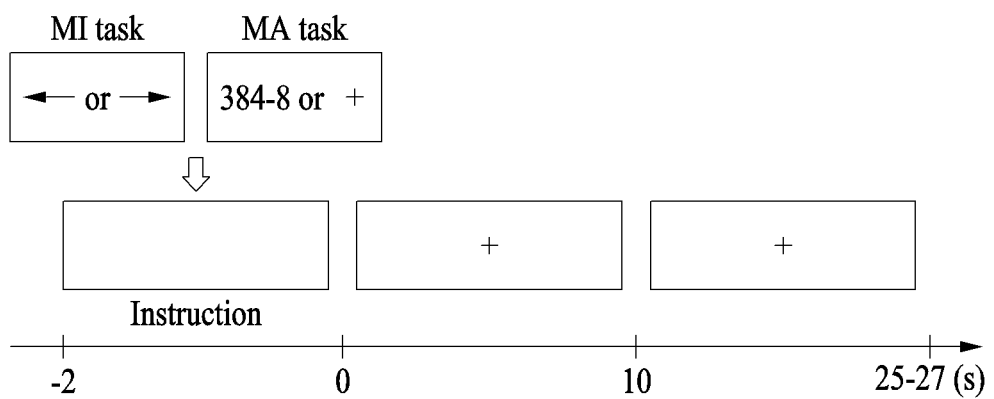
FIG. 9 is a diagram illustrating a paradigm of an experimental process according to an example embodiment.

Referring to FIGS. 8 to 10, the electronic device 100 of FIG. 1 or the training apparatus 300 of FIG. 2 may use the 1D EEG signal 310 and the 1D fNIRS signal 320 to generate a 3D EEG image or tensor, and a 3D fNIRS image or tensor, which will be described later. In an example embodiment, the EEG signal 310 and the fNIRS signal 320 collected by the training apparatus 300 may be included in an MA data set or an MI data set. For example, the EEG signal 310 and the fNIRS signal 320 included in the MA data set may be labeled as a baseline state or an MA task. For example, the EEG signal 310 and the fNIRS signal 320 included in the MI data set may be labeled as a left-hand MI task or a right-hand MI task.

For example, when the training apparatus 300 trains the neural network model 200 using the MA data set as training data, the training apparatus 300 may train the neural network model 200 to output a result 330 of determining whether brain activity measured by the EEG signal 310 and the fNIRS signal 320 relates to a baseline state or an MA task.

For example, when the training apparatus 300 trains the neural network model 200 using the MI data set as training data, the training apparatus 300 may train the neural network model 200 to output the result 330 of determining whether a brain activity measured by the EEG signal 310 and the fNIRS signal 320 relates to a left-hand MI task or a right-hand MI task.

In an example embodiment, the neural network model 200 may include an EEG branch 210, a fusion branch 220, and an fNIRS branch 230. In an example embodiment, the neural network model 200 may extract an EEG feature from an input EEG signal 310 using the EEG branch 210. In an example embodiment, the neural network model 200 may use the fusion branch 220 to extract a fusion feature based on the input EEG signal 310 and an input fNIRS signal 320. In an example embodiment, the neural network model 200 may extract an fNIRS feature from the input fNIRS signal 320 using the fNIRS branch 230.

In an example embodiment, the training apparatus 300 may output a first result by using the EEG feature extracted using the EEG branch 210, and output a second result by using the fusion feature extracted using the fusion branch 220. The training apparatus 300 may output the determination result 330 using a weighted sum of the first result and the second result.

In an example embodiment, the training apparatus 300 may calculate a loss 340 based on at least one of a classification loss 340, an fNIRS classification loss 340, and a correlation coefficient loss.

For example, the training apparatus 300 may calculate the classification loss 340 based on the determination result 330 and a labeling. For example, the training apparatus 300 may calculate a third result 330 using the fNIRS feature extracted from the fNIRS branch 230. For example, the training apparatus 300 may calculate the correlation coefficient loss of the EEG signal 310 and the fNIRS signal 320.

Figure 3:
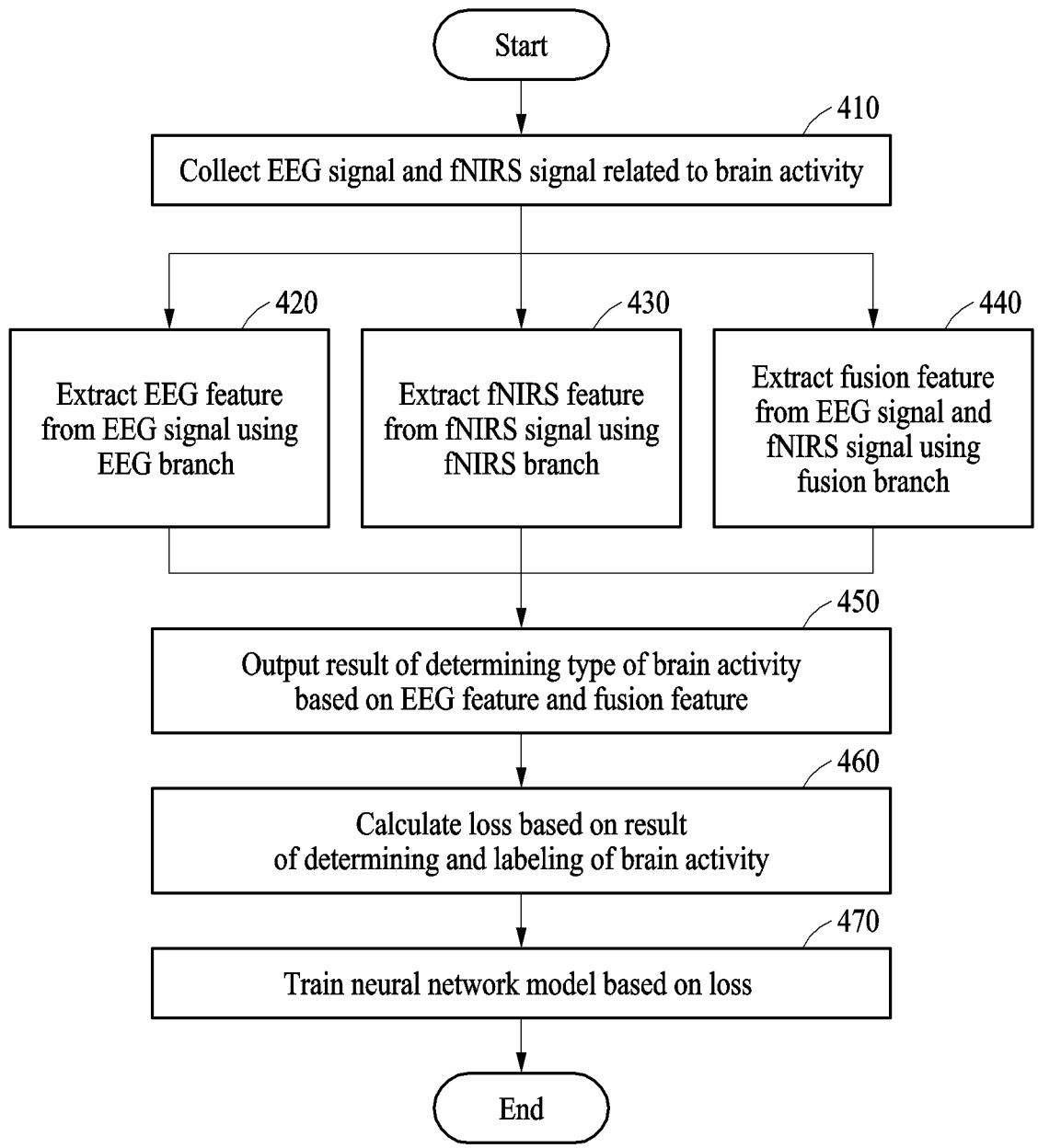
FIG. 3 is a diagram illustrating an operation of a neural network training method according to an example embodiment.

FIG. 3 is a diagram illustrating an operation of a neural network training method according to an example embodiment.

Referring to FIG. 3, the training apparatus 300 according to various example embodiments may collect an EEG signal 310 and an fNIRS signal 320 related to brain activity in operation 410. For example, the EEG signal 310 and the FNIRS signal 320 collected by the training apparatus 300 may be training data for training the neural network model 200.

For example, the EEG signal 310 and the FNIRS signal 320 collected by the training apparatus 300 may be included in an MA data set or an MI data set according to an instruction given to a measurement target. For example, the EEG signal 310 and the FNIRS signal 320 included in the MA data set may be labeled as a baseline state or an MA task. For example, the EEG signal 310 and the FNIRS signal 320 included in the MI data set may be labeled as a left-hand MI task or a right-hand MI task.

For example, when the measurement target is instructed to perform an MA task or an MI task, the EEG signal 310 and the FNIRS signal 320 may be measured simultaneously. The EEG signal 310 and the FNIRS signal 320 measured simultaneously may be treated as a pair.

In an example embodiment, the training apparatus 300 may extract an EEG feature from the EEG signal 310 using the EEG branch 210 in operation 420. For example, the EEG branch 210 may include at least one of a plurality of sequentially connected convolutional layers, a temporal attention pooling (TAP) layer, an FC layer, or a softmax layer.

For example, the training apparatus 300 may extract a first EEG feature by processing the EEG signal 310 using a convolutional layer. The training apparatus 300 may extract a second EEG feature by processing the first EEG feature using the convolutional layer. The training apparatus 300 may extract a third EEG feature by processing the second EEG feature using the convolutional layer. The training apparatus 300 may output an EEG feature by processing the third EEG feature according to a TAP layer and an FC layer.

In an example embodiment, in operation 430, the training apparatus 300 may extract an fNIRS feature from the FNIRS signal 320 using the fNIRS branch 230. For example, the fNIRS branch 230 may include at least one of a plurality of sequentially connected convolutional layers, a TAP layer, an FC layer, or a softmax layer.

For example, similar to the operation of extracting the first EEG feature, the second EEG feature, the third EEG feature, and the EEG feature from the EEG branch 210, the training apparatus 300 may extract a first fNIRS feature, a second fNIRS feature, a third fNIRS feature and an fNIRS feature.

In an example embodiment, the training apparatus 300 may extract a fusion feature from the EEG signal 310 and the FNIRS signal 320 using the fusion branch 220 in operation 440. For example, the fusion branch 220 may include at least one of a plurality of sequentially, connected convolutional layers, an FGA layer, a TAP layer, an FC layer, or a softmax layer. For example, the training apparatus 300 may extract a first fusion feature obtained by processing the EEG signal 310 using a convolutional layer. The training apparatus 300 may input the first EEG feature, the first fusion feature, and the first fNIRS feature to the FGA layer. The fusion feature output from the FGA layer may be input to a convolutional layer of a back-end of the FGA, and a second fusion feature may be output from the convolutional layer of the back-end of the FGA.

In the above-described example, the first fusion feature input to the FGA layer may be a fusion feature of a previous step, and the fusion feature (or FGA feature) output from the FGA layer may be a fusion feature of a next step.

In an example embodiment, the training apparatus 300 may extract a third fusion feature by processing the second EEG feature, the second fusion feature, and the second fNIRS feature according to the FGA layer and the convolutional layer. The description of the operation of the training apparatus 300 extracting the third fusion feature may be substantially the same as the description of the operation of the training apparatus 300 extracting the second fusion feature.

In an example embodiment, the training apparatus 300 may process the third EEG feature, the third fusion feature, and the third fNIRS feature using the FGA layer. The training apparatus 300 may output the fusion feature by processing the fusion feature output from the FGA layer according to the TAP layer and the FC layer.

In an example embodiment, in operation 450, the training apparatus 300 may output a result of determining a type of brain activity based on the EEG feature and the fusion feature. For example, the training apparatus 300 may output a first result and a second result by processing the EEG feature and the fusion feature according to the softmax layer, respectively. The training apparatus 300 may calculate a result as a weighted sum of the first result and the second result.

In an example embodiment, in operation 460, the training apparatus 300 may calculate a loss based on the result and labeling of the brain activity. For example, the training apparatus 300 may calculate a classification loss based on the result and the labeling. For example, the training apparatus 300 may process the fNIRS feature according to the softmax layer to output a third result. The training apparatus 300 may calculate an fNIRS classification loss (cross entropy loss) of the fNIRS branch 230 based on the third result and the labeling. For example, the training apparatus 300 may calculate a correlation coefficient loss of the EEG signal 310 and the FNIRS signal 320. For example, a loss may include at least one of a classification loss, an fNIRS classification loss, or a correlation coefficient loss.

In an example embodiment, the training apparatus 300 may train the neural network model 200 based on the loss in operation 470. For example, parameters, weights, and the like of the neural network model 200 may be updated to minimize a loss including at least one of a classification loss, an fNIRS classification loss, or a correlation coefficient loss.

Referring to operation 410 of FIG. 3, similarly, the electronic device (e.g., the electronic device 100 of FIG. 1) may collect the EEG signal 110 and the EEG signal 120. In operation 410, the training apparatus 300 may collect the EEG signal 310 and the FNIRS signal 320 for training the neural network model 200, and the electronic device 100 may collect the EEG signal 110 and the EEG signal 120 for determining a type of brain activity.

With respect to operations 420 to 450 of FIG. 3, the electronic device (e.g., the electronic device 100 of FIG. 1) may perform operations 410 to 450 in substantially the same manner. A description of the electronic device 100 for performing a method of determining brain activity is omitted. The description of the operation of the training apparatus 300 in operations 420 to 450 may substantially equally apply to the operation of the electronic device 100.

Figure 4:
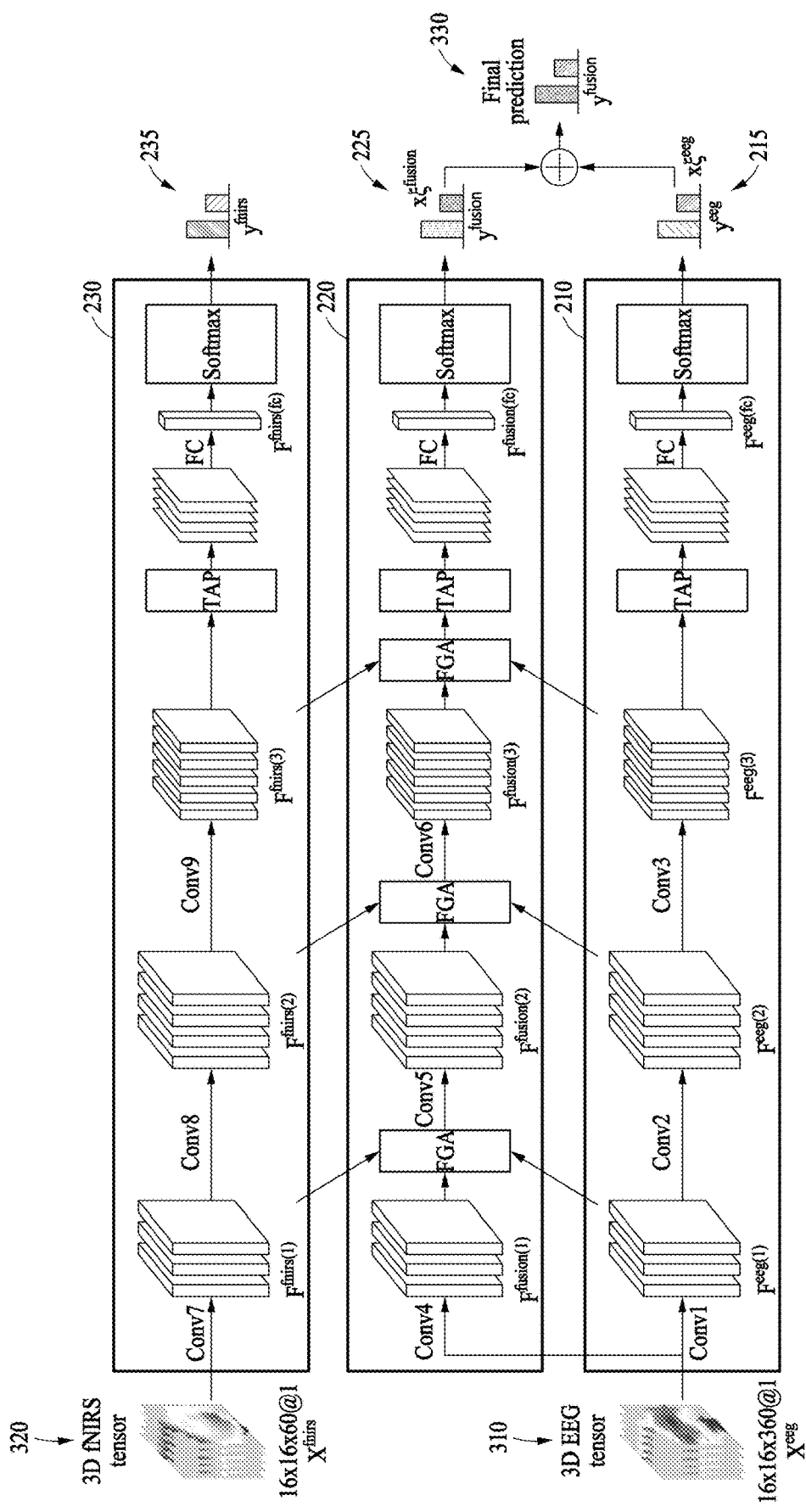
FIG. 4 is a diagram illustrating a neural network model including an electroencephalography (EEG) branch, a fusion branch, and a functional near-infrared spectroscopy (fNIRS) branch according to an example embodiment.

FIG. 4 is a diagram illustrating the neural network model 200 including the EEG branch 210, the fusion branch 220, and the fNIRS branch 230 according to an example embodiment.

Referring to FIG. 4, the neural network model 200 according to various example embodiments may include the EEG branch 210, the fusion branch 220, and the fNIRS branch 230.

In an example embodiment, the EEG branch 210 may include at least one of a plurality of sequentially connected convolutional layers, a TAP layer, an FC layer, or a softmax layer. For example, the EEG branch 210 may include a plurality of convolutional layers (e.g., Conv1, Conv2, and Conv3 of the EEG branch 210 of FIG. 4). For example, the neural network model 200 may use a first convolutional layer Conv1 of the EEG branch 210 to extract a first EEG feature $F^{eeg(1)}$ from input EEG signals 110 and 310 $X^{eeg}$. For example, the EEG signals 110 and 310 may have a size of 16×16×360@1.

For example, the neural network model 200 may use a second convolutional layer Conv2 of the EEG branch 210 to extract a second EEG feature $F^{eeg(2)}$ from the first EEG feature $F^{eeg(1)}$.

For example, the neural network model 200 may use a third convolutional layer Conv3 of the EEG branch 210 to extract a third EEG feature $F^{eeg(3)}$ from the second EEG feature $F^{eeg(2)}$.

In an example embodiment, the neural network model 200 may process the third EEG feature $F^{eeg(3)}$ of the EEG branch 210 using a TAP layer and an FC layer to extract an EEG feature $F^{eeg(fc)}$ For example, the TAP layer may be a layer that is compressed by a time axis of a feature among height, width, time, and channel dimensions of an input feature. A configuration and operation of the TAP layer will be described below with reference to FIG. 5. In an example embodiment, the neural network model 200 may output a first result 215 $y^{eeg}$ based on the EEG feature $F^{eeg(fc)}$ using the EEG branch 210. For example, the neural network model 200 may process the EEG feature $F^{eeg(fc)}$ using a softmax layer to output the first result 215 $y^{eeg}$.

In an example embodiment, the fNIRS branch 230 may include at least one of a plurality of sequentially connected convolutional layers, a TAP layer, an FC layer, or a softmax layer.

For example, the fNIRS branch 230 may include a plurality of convolutional layers (e.g., Conv7, Conv8, and Conv9 of the fNIRS branch 230 of FIG. 4). For example, the neural network model 200 may use a seventh convolutional layer Conv7 of the fNIRS branch 230 to extract a first fNIRS feature $F^{fnirs(1)}$ from input fNIRS signals 120 and 320 $X^{fnis}$. For example, the fNIRS signals 120 and 320 may have a size of 16×16×60@1.

For example, the neural network model 200 may use an eighth convolutional layer Conv8 of the fNIRS branch 230 to extract a second fNIRS feature $F^{fnirs(2)}$ from the first fNIRS feature $F^{fnirs(1)}$.

For example, the neural network model 200 may use a third convolutional layer Conv3 of the EEG branch 210 to extract a third fNIRS feature $F^{fnirs(3)}$ from the second fNIRS feature $F^{fnirs(2)}$.

In an example embodiment, the neural network model 200 may process the third fNIRS feature $F^{fnirs(3)}$ of the fNIRS branch 230 using a TAP layer and an FC layer to extract an fNIRS feature $F^{fnirs(fc)}$.

In an example embodiment, the neural network model 200 may output a third result 235 $y^{fnirs}$ based on the fNIRS feature $F^{fnirs(fc)}$ using the fNIRS branch 230. For example, the neural network model 200 may process the fNIRS feature $F^{fnirs(fc)}$ using a softmax layer to output the third result 235 $y^{fnirs}$.

In an example embodiment, the fusion branch 220 may include at least one of a plurality of sequentially connected convolutional layers, an FGA layer, a TAP layer, an FC layer, or a softmax layer.

For example, the fusion branch 220 may include a plurality of convolutional layers (e.g., Conv4, Conv5, and Conv6 of the fusion branch 220 of FIG. 4). For example, the neural network model 200 may use a fourth convolutional layer Conv4 of the fusion branch 220 to extract a first fusion feature $F^{fusion(1)}$ from input EEG signals 110 and 310 $X^{eeg}$. For example, the EEG signals 110 and 310 may have a size of 16×16×360@1.

For example, the neural network model 200 may use an FGA layer of the fusion branch 220 to output a fusion feature of a next step using an input EEG feature, a fusion feature of a previous step, and an fNIRS feature. A configuration and operation of an FGA layer outputting a fusion feature of a next step will be described below with reference to FIGS. 6 and 7.

For example, the fusion feature of the previous step may be output from a convolutional layer of a front-end of the FGA layer, and the fusion feature of the next step may be input to a convolutional layer or a TAP layer of a back-end of the FGA layer. For example, the fusion feature of the previous step may be $F^{fusion(1)}$, $F^{fusion(2)}$, $F^{fusion(3)}$ output from the convolutional layers Conv4, Conv5, and Conv6 of the fusion branch 220. For example, the fusion feature of the next step may be $\hat{F}^{fusion(1)}$, $\hat{F}^{fusion(2)}$ $\hat{F}^{fusion(3)}$ output from the FGA layer of the fusion branch 220. For example, $\hat{F}^{fusion(1)}$, $\hat{F}^{fusion(2)}$, $\hat{F}^{fusion(3)}$ output from the FGA layer may be a first FGA feature, a second FGA feature, and a third FGA feature, respectively.

For example, the neural network model 200 may use the FGA layer of the fusion branch 220 to output the fusion feature $\hat{F}^{fusion(1)}$ of the next step using an input first EEG feature $F^{eeg(1)}$, the fusion feature $F^{fusion(1)}$ of the previous step, and the first fNIRS feature $F^{fnirs(1)}$ For example, the neural network model 200 may use a fifth convolutional layer Conv5 of the fusion branch 220 to extract a second fusion feature $F^{fusion(2)}$ from the first FGA feature $\hat{F}^{fusion(1)}$.

For example, the neural network model 200 may use the FGA layer of the fusion branch 220 to output the fusion feature $\hat{F}^{fusion(2)}$ of the next step. For example, the neural network model 200 may output the fusion feature $\hat{F}^{fusion(2)}$ of the next step by processing the second EEG feature $F^{eeg(2)}$, the second fusion feature $F^{fusion(2)}$ that is the fusion feature of the previous step, and the second fNIRS feature $F^{fnirs(2)}$ through the FGA layer.

For example, the neural network model 200 may use a sixth convolutional layer Conv6 of the fusion branch 220 to extract a third fusion feature $F^{fusion(3)}$ from the second FGA feature $\hat{F}^{fusion(2)}$.

For example, the neural network model 200 may use the FGA layer of the fusion branch 220 to output the fusion feature $\hat{F}^{fusion(3)}$ of the next step. For example, the neural network model 200 may output the fusion feature $\hat{F}^{fusion(3)}$ of the next step by processing the third EEG feature $F^{eeg(3)}$, the third fusion feature $F^{fusion(3)}$ that is the fusion feature of the previous step, and the third fNIRS feature $F^{fnirs(3)}$. through the FGA layer.

In an example embodiment, the neural network model 200 may output a fusion feature $F^{fusion(fc)}$ by processing a third FGA feature $\hat{F}^{fusion(3)}$ output from an FGA layer of a last part of the fusion branch 220 using a TAP layer and an FC layer.

In an example embodiment, the neural network model 200 may output a second result 225 $y^{fusion}$ based on a fusion feature $F^{fusion(fc)}$ in the fusion branch 220. For example, the neural network model 200 may process the fusion feature $F^{fusion(fc)}$ using a softmax layer to output the second result 225 $y^{fusion}$.

In an example embodiment, the neural network model 200 may output the result 330 of determining a type of brain activity corresponding to the EEG signals 110 and 310 and the fNIRS signals 120 and 320 based on an EEG feature and a fusion feature. For example, the neural network model 200 may output the first result 215 and the second result 225 by processing each of the EEG feature and the fusion feature through the softmax layer.

For example, the neural network model 200 may output the result 330 by applying a weight assigned to each of the first result 215 and the second result 225. For example, the neural network model 200 may output the result 330 $y^{pred}$ using a weight $\xi^{eeg}$ assigned to the first result 215 $y^{eeg}$ and a weight $\xi^{fusion}$ assigned to the second result 225 $y^{fusion}$, as shown in Equation 1 below. As shown in Equation 1 below, the neural network model 200 may calculate the result 330 as a weighted sum of the first result 215 and the second result 225.

$$y^{pred}=\xi^{eeg}y^{eeg}+\xi^{fusion}y^{fusion} \quad \text{[Equation 1]}$$

In Equation 1 above, $y^{eeg} \in \mathbb{R}^2$ may denote the first result 215, for example, a prediction score of the EEG branch 210, $y^{fusion} \in \mathbb{R}^2$ may denote the second result 225, for example, a prediction score of the fusion branch 220, and $y^{pred}$ may denote the result 330, for example, a final prediction score.

In an example embodiment, a prediction weight vector $\xi=[\xi^{eeg}, \xi^{fusion}]$ may be calculated as shown in Equation 2 below.

$$\xi=\sigma_{Soft}(FC^{2\times 1}([F^{eeg},F^{fusion}])) \quad \text{[Equation 2]}$$

In Equation 2 above, $F^{eeg}$ may denote an EEG feature, for example, an output of an FC layer of the EEG branch 210, $F^{fusion}$ may denote a fusion feature, for example, an output of an FC layer of the fusion branch 220, [•] may denote a concatenation function for a first dimension. For example, $F^{eeg}$, $F^{fusion}$ may be $\in \mathbb{R}^{64\times 1}$.

The fusion branch 220 may extract a joint representation from the EEG feature and the fNIRS feature. There may be an inherent delay related to the fNIRS signals 120 and 320 compared to the EEG signals 110 and 310. For example, when the training apparatus 300 trains the neural network model 200 of FIG. 4, decoding performance may be degraded due to a delay of the fNIRS signals 120 and 320 that occurred when the training began. For example, the training apparatus 300 may prevent performance degradation of the fusion branch 220 by calculating the result 330 $y^{pred}$ as shown in Equations 1 and 2 above.

Table 1 below shows a structure of the neural network model 200 of FIG. 4. The descriptions of the convolutional layers Conv1, Conv2, and Conv3 of the EEG branch 210 of Table 1 below may equally apply to the convolutional layers Conv4, Conv5, and Conv6 of the fusion branch 220 and the convolutional layers Conv7, Conv8, and Conv9 of the fNIRS branch 230, respectively. For example, the description of Conv1 may equally apply to Conv4 or Conv7, the description of Conv2 may equally apply to Conv5 or Conv8, and the description of Conv3 may equally apply to Conv6 or Conv9.

TABLE 1

| Layer | Kernal Filter size | Kernal Stride | Kernal Channel | Output Dimension |
|---|---|---|---|---|
| Input |  |  |  | 16 × 16 × 60 × 1 |
| Conv1 | 2 × 2 × 9 | 2 × 2 × 2 | 16 | 8 × 8 × 30 × 16 |
| Conv2 | 2 × 2 × 3 | 2 × 2 × 2 | 32 | 4 × 4 × 15 × 32 |

TABLE 1-continued

| Layer | Kernal Filter size | Kernal Stride | Kernal Channel | Output Dimension |
|---|---|---|---|---|
| Conv3 | 2 × 2 × 3 | 2 × 2 × 2 | 64 | 2 × 2 × 8 × 64 |
| TemporalAP |  |  |  | 2 × 2 × 1 × 64 |
| FC | 256 × 64 |  |  | 1 × 64 |
| Dropout |  |  |  | 1 × 64 |
| Softmax | 64 × 2 |  |  | 2 |

The convolutional layers Conv1 to Conv9 of FIG. 4 may be 3D convolutional layers and may have a rectified linear unit activation function. The convolutional layers Conv1 to Conv9 may extract spatial information from a 3D EEG tensor or a 3D fNIRS tensor.

For example, a feature input to a convolutional layer may be down-sampled by a stride of the convolutional layer.

In order to increase non-linearity with a small parameter, a small kernel size of (2×2×3) and a stride of (2×2×2) may be applied, as shown in Table 1. Since a time dimension is greater than a spatial dimension, a kernel size of (2×2×9) and a stride of (2×2×2) may be applied in a first convolutional layer (e.g., Conv1, Conv4, and Conv7 in FIG. 4). In an example embodiment, a size of the kernel and the stride may be determined through an optimization process.

For example, the TAP layer may efficiently compress spatial information of a 3D feature. A feature in which spatial information is compressed through the TAP layer may be classified through the FC layer and the softmax layer having a ReLU function. For example, to prevent overfitting, a dropout (e.g., the dropout in Table 1) may be applied to an output of the FC layer.

In an example embodiment, the training apparatus 300 may calculate a loss using the neural network model 200 of FIG. 4. For example, the training apparatus 300 may calculate the loss using at least one of a classification loss, an fNIRS classification loss, or a correlation coefficient loss.

For example, the training apparatus 300 may calculate a loss L as shown in Equation 3 below.

$$L=L_{class}+L_{fnirs}+\lambda L_{fga}, \quad \text{[Equation 3]}$$

In Equation 3 above, $L_{class}$ may denote a classification loss, $L_{fnirs}$ may denote an fNIRS classification loss, $L_{fga}$ may denote a correlation coefficient loss, and $\lambda$ may denote a regularization parameter greater than 0.

A training target of the neural network model 200 according to an example embodiment may be to interpret brain activity from the EEG signals 110 and 310 and the fNIRS signals 120 and 320, and a cross-entropy function may be applied to the result 330 output from the neural network model 200 as shown in Equation 4 below.

$$L_{class}=-\frac{1}{N}\sum_{i=1}^{N}y_i \cdot \log(y^{pred}(X_i)) \quad \text{[Equation 4]}$$

$y_i$ may denote labeling of an i-th input $X_i=\{X_i^{eeg},X_i^{fnirs}\}$ $y^{pred}(X_i)$ may denote, the result 330 (or a prediction score) output from the neural network model 200 for an input $X_i$, • may denote a dot product, and NV may denote a number of input data (e.g., training data).

Since the FGA layer extracts an FGA map (or an attention map) for identifying a spatially significant region from the fNIRS features of the fNIRS branch 230, the performance of the neural network model 200 may depend on how well the fNIRS features capture exclusive features between classes.

In the training of the neural network model 200, in order to accelerate a training process of the fNIRS branch 230, an fNIRS classification loss function which maximizes classification accuracy and minimizes classification error of fNIRS data may be applied to calculate the fNIRS classification loss $L_{fnirs}$ as shown in Equation 5 below.

$$L_{fnirs} = -\frac{1}{N}\sum_{i=1}^{N} y_i \cdot \log\left(y^{fnirs}\left(X_i^{fnirs}\right)\right) \quad \text{[Equation 5]}$$

In Equation 5 above, $y^{fnirs}(X_i^{fnirs})$ may denote a prediction score of the fNIRS branch 230 for an input $X_i^{fnirs}$, for example, the third result 235 output from the fNIRS branch 230 of FIG. 4.

The FGA map (or the attention map) $\Phi$ output from the FGA layer may be for highlighting a spatially significant region of an EEG feature based on an fNIRS feature, and improving classification performance. A metric may be required for measuring a spatial association between an EEG feature and an fNIRS feature. For example, a Pearson correlation coefficient (PCC) for training the FGA map to maximize a correlation between two signals defined as in Equation 6 below may be used.

$$PCC(U,V) = \frac{\sum_{i,j}(U_{i,j} - \overline{U})(V_{i,j} - \overline{V})}{\sqrt{\sum_{i,j}(U_{i,j}-\overline{U})}\sqrt{\sum_{i,j}(V_{i,j}-\overline{V})}} \quad \text{[Equation 6]}$$

In Equation 6 above, $\overline{U}$, $\overline{V}$ may, denote a mean of all elements of each matrix $U$, $V \in \mathbb{R}^{H \times W}$.

In an example embodiment, a PCC between an EEG feature and an FGA map may be maximized according to Equations 7 and 8 below.

$$L_{fga} = -\frac{1}{N}\sum_{i=1}^{N}\sum_{l=1}^{3} PCC\left(\tilde{F}^{eeg(l)}(X_i^{eeg}), \Phi^{(l)}(X_i^{fnirs})\right) \quad \text{[Equation 7]}$$

$$\tilde{F}_{h,w} = \frac{1}{TC}\sum_{t'=1}^{T}\sum_{c'=1}^{C} F_{h,w,t',c'} \quad \text{[Equation 8]}$$

$F^{eeg(l)}$, $\Phi^{(l)}$ may denote an EEG feature and an FGA map of an l-th layer, respectively. In order to compress the EEG feature in temporal and channel dimensions, the EEG feature may be averaged in the corresponding dimensions.

In an example embodiment, FGA map regularization based on a PCC may interfere with the training of the EEG branch 210 in a training process of the neural network model 200 since the performance of the fNIRS branch 230 may be significantly lower than that of the EEG branch 210, and there may be an inherent response delay related to the fNIRS signals 120 and 320. In an example embodiment, in a process of the training apparatus 300 training the neural network model 200, to maintain the performance of the EEG branch 210, a gradient flow to the EEG branch 210 directed in FGA map regularization (e.g., maximization of the correlation coefficient loss according to Equations 7 and 8) may be blocked.

In an example embodiment, the training apparatus 300 of FIG. 2 may train the neural network model 200 of FIG. 4. For example, the training apparatus 300 may input training data (e.g., an MA data set or an MI data set), output the result 330, and calculate a loss. The training apparatus 300 may train the neural network model 200 to minimize loss.

In an example embodiment, the electronic device 100 of FIG. 1 may use the neural network model 200 of FIG. 4 to output the result 130 of determining brain activity related to collected EEG signals 110 and 310 and the fNIRS signals 120 and 320. For example, the neural network model 200 used by the electronic device 100 may be the neural network model 200 trained by the training apparatus 300 of FIG. 2.

Figure 5:
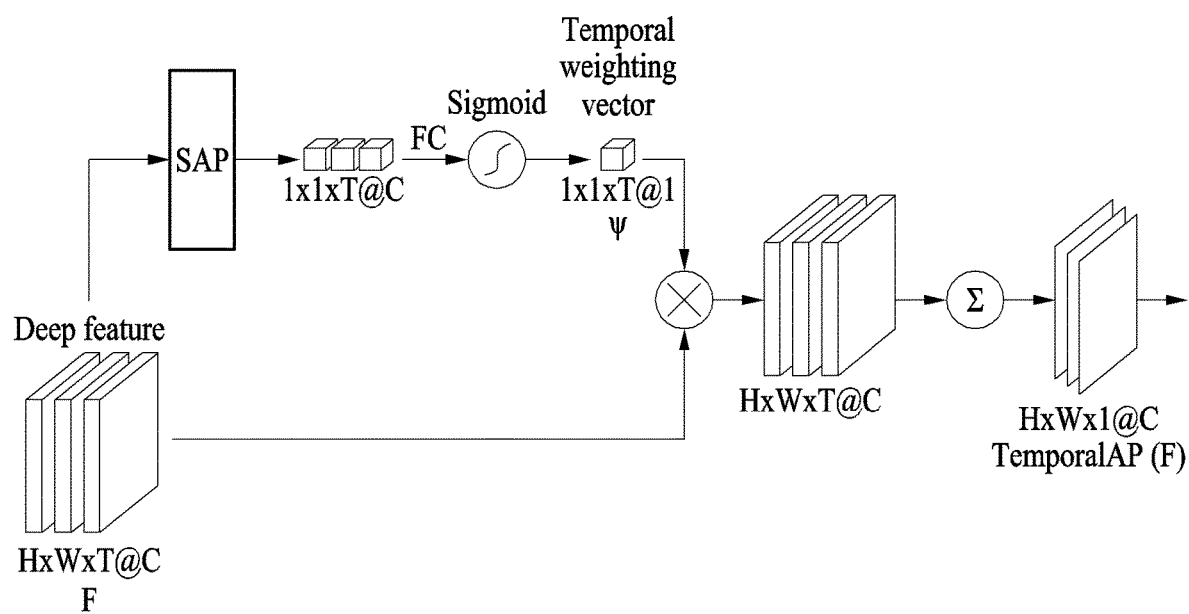
FIG. 5 is a diagram illustrating a temporal attention pooling (TAP) layer according to an example embodiment.

FIG. 5 is a diagram illustrating a TAP layer according to an example embodiment.

In an example embodiment, a TAP layer may compress a time dimension of an input feature (e.g., a deep feature of FIG. 5). For example, a 3D deep feature input to the TAP layer may have height and width dimensions, and time and channel dimensions.

For example, in 3D features (e.g., first to third EEG features, first to third fNIRS features, first to third fusion features, EEG signals 110 and 310, fNIRS signals 120 and 320, and the like) $F \in \mathbb{R}^{H \times W \times T \times C}$, H and W may denote a height and a width, respectively, T may denote a total time step, and C may denote a number of channels including time information.

Brain activity may change significantly over time while a task is being performed. Accordingly, brain signals (e.g., EEG signals 110 and 310 or fNIRS signals 120 and 320) may have a task-related segment at a predetermined time index during a task period. For example, a difference in spectral power according to a cognitive load may appear 1 to 2 seconds after stimulation, and may vary depending on a subject. Therefore, it may be important to assign a large weight to a task-related time segment.

In an example embodiment, an operation according to the TAP layer of FIG. 5 may be described by Equations 9 to 11 below. The TAP layer may compress a T channel of an input 3D feature such as, TAP: $\mathbb{R}^{H \times W \times T \times C} \to \mathbb{R}^{H \times W \times 1 \times C}$.

$$TAP(F)_{h,w,1,c} = \sum_{t'} \psi_{t'} F_{h,w,t',c} \quad \text{[Equation 9]}$$

In Equation 9 above, $F_{h,w,t,c}$ may denote components h, w, t, c of feature F, and $\psi \in \mathbb{R}^{T \times 1}$ may denote a temporal weight vector that may be determined according to an input signal.

In order to obtain the temporal weight vector of Equation 9, as shown in FIG. 5, a 3D feature F may be processed using a SAP layer to be spatially reduced, and be input to an FC layer together with a softmax function. For example, the temporal weight vector $\psi$ may be obtained as shown in Equations 10 and 11 below.

$$\psi = \sigma_{soft}(FC^{T \times 1}(SAP(F))) \quad \text{[Equation 10]}$$

$$SAP(F)_{1,1,t,c} = \sum_{h',w'} \Theta_{h',w'} F_{h',w',t,c} \quad \text{[Equation 11]}$$

In Equations 10 and 11 above, $\sigma_{soft}(\bullet)$ may denote a softmax function, $FC^{T \times 1}(\bullet)$ may denote an FC layer with an output of a size of T×1, $\Theta \in \mathbb{R}^{H \times W}$ may denote a trainable parameter for an SAP layer.

For example, the SAP layer may compress a spatial domain of an input 3D feature by weighting a task-related brain region.

Figure 6:
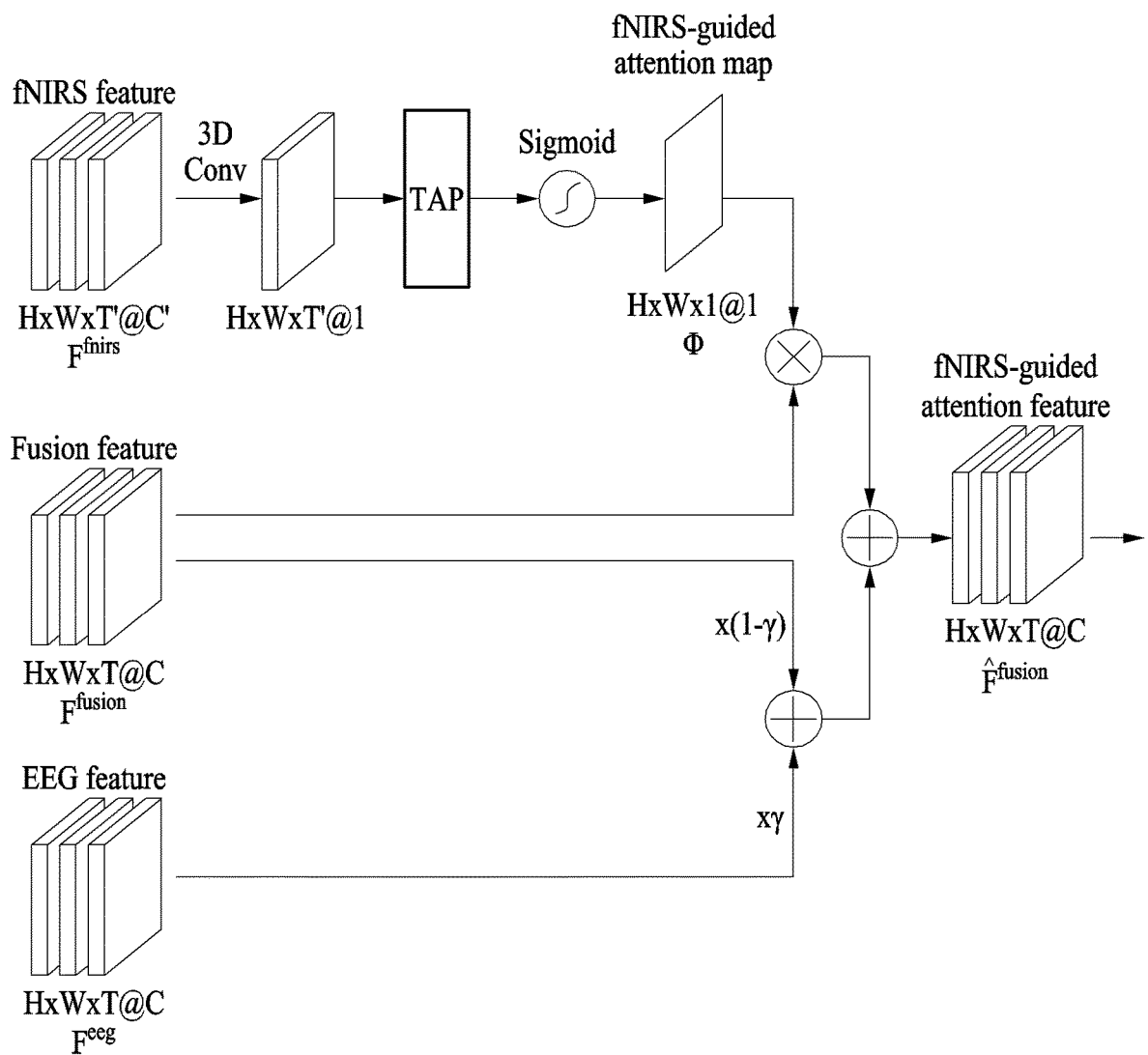
FIG. 6 is a diagram illustrating an fNIRS-guided attention (FGA) layer according to an example embodiment.

FIG. 6 is a diagram illustrating an FGA layer according to an example embodiment.

Referring to FIG. 6, an EEG feature $F^{eeg}$, a fusion feature $F^{fusion}$, and an fNIRS feature $F^{fnirs}$ may be input to an FGA layer, and the FGA layer may output an FGA feature.

For example, a fusion feature $F^{fusion}$ input to an FGA layer may be a fusion feature of a previous step, and may be a fusion feature output from a convolutional layer (e.g., Conv4, Conv5, Conv6 of FIG. 4) of a front-end of the FGA layer. For example, a fusion feature $\hat{F}^{fusion}$ output from an FGA layer may be a fusion feature of a next step, and may be a convolutional layer (e.g., Conv5, Conv6 of FIG. 4) of a back-end of the FGA layer or a fusion feature input to the TAP layer.

For example, a fusion branch (e.g., the fusion branch 220 of FIG. 2 and the fusion branch 220 of FIG. 4) may include an FGA layer as shown in FIG. 6. For example, the FGA layer may extract a joint representation of a 3D EEG feature and a 3D fNIRS feature based on neurovascular coupling. For example, EEG signals 110 and 310 and fNIRS signals 120 and 320 may be strongly correlated in a spatial dimension because activation of brain activity in a predetermined brain region may promote both cortical currents and blood flow.

In an example embodiment, an output of the FGA layer $\hat{F}^{fusion}$ may be calculated as shown in Equation 12 below. According to Equation 12 below, in an output $\hat{F}^{fusion}$ of the FGA layer, an EEG feature $\gamma F_{h,w,t,c}^{eeg}$ according to a residual parameter and a fusion feature $(1-\gamma)F_{h,w,t,c}^{fusion}$ of a previous step may be reflected in an output $\hat{F}^{Fusion}$, and a value obtained by multiplying an FGA map $\Phi_{h,w,1,1}$ by a fusion feature of a previous step $F^{Fusion}$ may be reflected in an output $\hat{F}^{fusion}$.

The FGA layer may output a fusion feature (or an FGA feature) $\hat{F}^{Fusion}$ of a next step by processing an EEG feature $F_{h,w,t,c}^{eeg}$ and a fusion feature $F^{fusion}$ of a previous step based on an FGA map $\Phi_{h,w,1,1}$ output based on an fNIRS feature and a residual parameter γ as shown in Equation 12 below.

$$\hat{F}_{h,w,t,c}^{Fusion} = \gamma F_{h,w,t,c}^{eeg} + (1-\gamma)F_{h,w,t,c}^{fusion}\alpha\Phi_{h,w,1,1}F_{h,w,t,c}^{fusion} \quad \text{[Equation 12]}$$

In Equation 12 above, γ· may denote a residual parameter of 0 or more and 1 or less, and $\Phi \in \mathbb{R}^{H \times W \times 1 \times 1}$ may denote an FGA map. For example, an FGA map Φ may denote a spatial weight matrix extracted from the fNIRS signals 120 and 320, and may be calculated as shown in Equation 13 below.

$$\Phi = \sigma_{sig}(TAP(f^{3 \times 3 \times 3 @ 1}(F^{fnirs}))) \quad \text{[Equation 13]}$$

In Equation 13, $f^{3 \times 3 \times 3 @ 1}$ may represent a convolutional layer with a filter size of 3×3×3 and having one output filter, and $f^{3 \times 3 \times 3 @ 1}$ may extract an attention feature in a channel dimension from a 3D fNIRS feature.

Referring to Equation 13 and FIG. 6, the TAP layer included in the FGA layer may assign a large weight to a temporally important time segment.

For example, an FGA map (or an attention map) Φ may not be fixed, and may be determined according to each fNIRS input. The FGA map Φ may lead to a reliable attention for a spatially significant region, but with an unexpectedly low-weight spatial attention there may be a loss of information in the corresponding region. In an example embodiment, as shown in FIG. 6, an EEG feature of the EEG branch 210 may be input to the FGA layer to alleviate information loss of the EEG feature. A residual parameter γ· may be determined by a trainable parameter $\gamma_{train}$ and a sigmoid function $\sigma_{sig}$, and may be calculated by a residual parameter $\gamma = \sigma_{sig}(\gamma_{train})$.

In an example embodiment, the residual parameter may be optimized according to the performance of the neural network model 200. Table 2 below shows the classification accuracy of an MA task and an MI task of an entire neural network model (e.g., the neural network model 200 of FIG. 4) according to the residual parameter γ·.

TABLE 2

| Task | γ | Mean Acc (%) | Max Acc (%) |
|---|---|---|---|
| MA task | 0 | 91.32 ± 06.59 | 94.60 ± 06.62 |
|  | 0.3 | 91.24 ± 05.58 | 94.14 ± 06.79 |
|  | 0.5 | 92.29 ± 06.27 | 95.69 ± 05.97 |
|  | 0.7 | 91.66 ± 05.97 | 94.71 ± 05.47 |
|  | 1.0 | 91.21 ± 05.99 | 94.37 ± 05.87 |
|  | $\gamma_{train}$ | 91.96 ± 05.82 | 95.46 ± 05.12 |
| MI task | 0 | 77.93 ± 08.66 | 79.60 ± 10.58 |
|  | 0.3 | 78.36 ± 09.04 | 80.29 ± 09.62 |
|  | 0.5 | 78.72 ± 08.50 | 80.29 ± 10.28 |
|  | 0.7 | 77.43 ± 08.86 | 78.74 ± 10.25 |
|  | 1.0 | 77.94 ± 08.63 | 79.43 ± 09.61 |
|  | $\gamma_{train}$ | 78.59 ± 08.86 | 80.23 ± 09.63 |

For example, in Equation 12, when the residual parameter γ· is 0 or 1, respectively, an output of the last FGA layer may be expressed by Equation 14 or Equation 15 below.

$$\hat{F}_{h,w,t,c}^{fusion(3)} = F_{h,w,t,c}^{fusion(3)} + \Phi_{h,w,1,1}F_{h,w,t,c}^{fusion(3)} \text{ if } \gamma=0 \quad \text{[Equation 14]}$$

$$\hat{F}_{h,w,t,c}^{fusion(3)} = F_{h,w,t,c}^{eeg(3)} + \Phi_{h,w,1,1}F_{h,w,t,c}^{fusion(3)} \text{ if } \gamma=0 \quad \text{[Equation 15]}$$

In Equation 14, when the residual parameter γ· is 0, the EEG feature may not be used in the fusion branch 220. In Equation 15, when the residual parameter is γ·1, the fusion feature of the previous step in the fusion branch 220 may not be added to the FGA layer. According to Table 2, when the residual parameter γ· is 0.5, the classification accuracy of the neural network model 200 may be higher than when the residual parameter γ· is 0 or 1.

An appropriate residual EEG feature may adjust EEG information in the fusion branch 220 to significantly improve performance. Considering that the performance of the neural network model 200 is higher when the residual parameter is 0<γ·<1 compared to when the residual parameter is 1, it may be confirmed that an early fusion feature has a higher potential for performance improvement compared to a late fusion feature.

Figure 7:
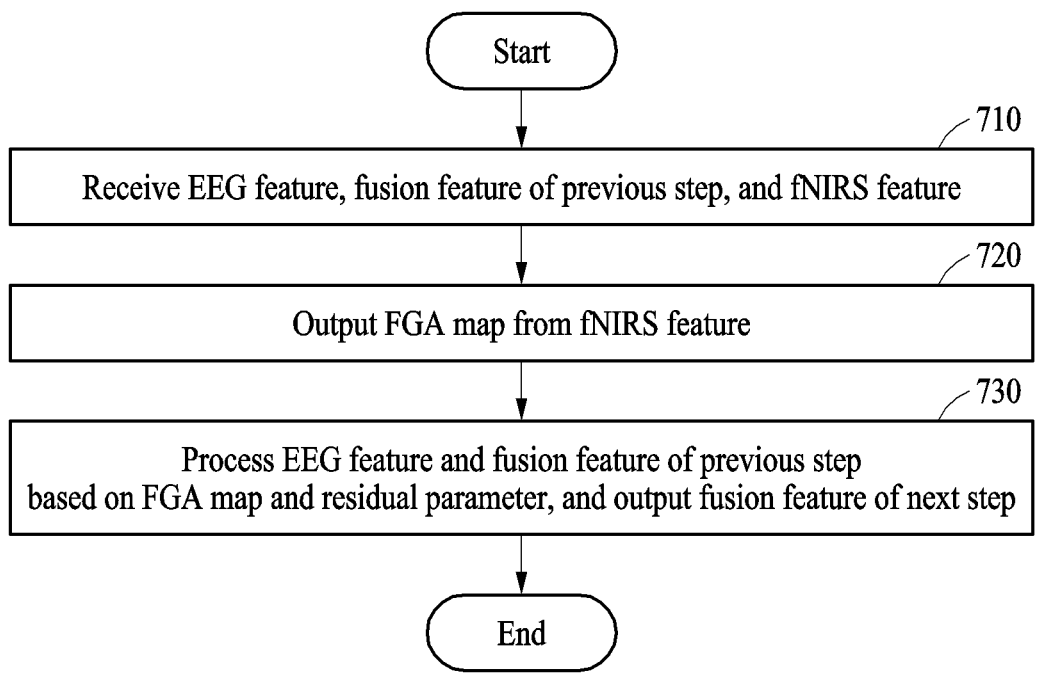
FIG. 7 is a diagram illustrating an operation of an FGA layer according to an example embodiment.

FIG. 7 is a diagram illustrating an operation of an FGA layer according to an example embodiment.

Referring to FIG. 7, an FGA layer according to various example embodiments may receive an EEG feature, a fusion feature of a previous step, and an fNIRS feature in operation 710. For example, the fusion feature of the previous step may be an output of a convolutional layer of a front-end of the FGA layer.

For example, the EEG feature and the fNIRS feature input to the FGA layer may be an output of a convolutional layer of the EEG branch 210 and the fNIRS branch 230 corresponding to the FGA layer, respectively. For example, in FIG. 4, the EEG feature output from Conv1 of the EEG branch 210 and the fNIRS feature output from Conv7 of the fNIRS branch 230 may be input to a first FGA layer of the fusion branch 220.

In an example embodiment, the FGA layer may output an FGA map from the fNIRS feature in operation 720. For example, the FGA map may be a map in which a significant region is extracted from a spatial region in which brain activity is measured from the fNIRS signals 120 and 320. For example, the FGA layer may improve performance of the entire neural network model 200 by processing the EEG feature according to the FGA map.

For example, the FGA layer may output the FGA map by processing input fNIRS signals 120 and 320 according to a 3D convolutional layer, a TAP layer, and a sigmoid function.

In an example embodiment, in operation 730, the FGA layer may process the EEG feature and the fusion feature of the previous step based on the FGA map and a residual parameter, and output a fusion feature of a next step. For example, the fusion feature of the next step may be input to the convolutional layer or the TAP layer of a back-end of the FGA layer.

For example, the FGA layer may output the fusion feature of the next step by adding a value obtained by multiplying the FGA map by the fusion feature of the previous step and a reflection ratio for the fusion feature of the previous step and the EEG feature according to the residual parameter.

FIG. 8 is a diagram illustrating an EEG electrode 810, an fNIRS source 830, and an fNIRS detector 840 according to an example embodiment. FIG. 9 is a diagram illustrating a paradigm of an experimental process according to an example embodiment.

The EEG electrode 810, an EEG ground 820, the fNIRS source 830, the fNIRS detector 840, and an fNIRS channel 850 may be attached to a measurement target as shown in FIG. 8, such that the electronic device 100 or the training apparatus 300 may collect an EEG signal (e.g., the EEG signal 110 of FIG. 1 or the EEG signal 310 of FIG. 3) and an fNIRS signal (e.g., the fNIRS signal 120 of FIG. 1 or the fNIRS signal 320 of FIG. 3).

In an example embodiment, the EEG signals 110 and 310 may be collected from 30 channels at 1000 Hz, and the fNIRS signals 120 and 320 may be collected from 36 channels at 12.5 Hz. The collected EEG signals 110 and 310 and fNIRS signals 120 and 320 may be down-sampled to 200 Hz and 10 Hz, respectively.

As shown in FIG. 9, the measurement target may perform a baseline state which is to be in a resting state, an MA task, and a left-hand or right-hand MI task. The MA task may be the measurement target repeatedly performing an operation of subtracting a single digit from a three-digit number in a task period. The MI task may be the measurement target repeatedly imagining opening and closing a hand in the task period.

Measurement of the EEG signals 110 and 310 and the fNIRS signals 120 and 320 may be performed in a task period of 10 seconds and a baseline period of 15 to 17 seconds, after an instruction period of 2 seconds indicating the MI task or the MA task. The length of the baseline period between 15 and 17 seconds may be chosen arbitrarily.

For example, the MA task or the MI task may be measured by repeating an instruction period (e.g., 2 seconds), a task period (e.g., 10 seconds), and a baseline period (e.g., 15 seconds to 17 seconds).

The EEG signals 110 and 310 may be referenced back to a common average reference, filtered from 0.5 Hz to 50 Hz, and then down-sampled to 120 Hz. Thereafter, electrooculography (EOG) artifacts may be removed by an independent component analysis (ICA).

In an example embodiment, a data set may be divided into two data sets for training the neural network model 200. For example, the data set may be divided into an MA data set and an MI data set, the MA data set may be divided according to a baseline state and an MA task, and the MI dataset may be divided according to a left-hand MI task and a right-hand MI task.

A data set for training the neural network model 200, for example, an MA data set and an MI data set, may crop a 10-second task period to a 3-second task period. The EEG signals 110 and 310 and the fNIRS signals 120 and 320 of the MA data set and the MI data set may be 3 seconds long and have a time step of 1 second.

For example, sizes of the EEG signals 110 and 310 and the fNIRS signals 120 and 320 of the MA data set and the MI data set may be 30×360 (number of EEG channels X time) and 36×360 (number of fNIRS channels X time), respectively.

Figure 10A:
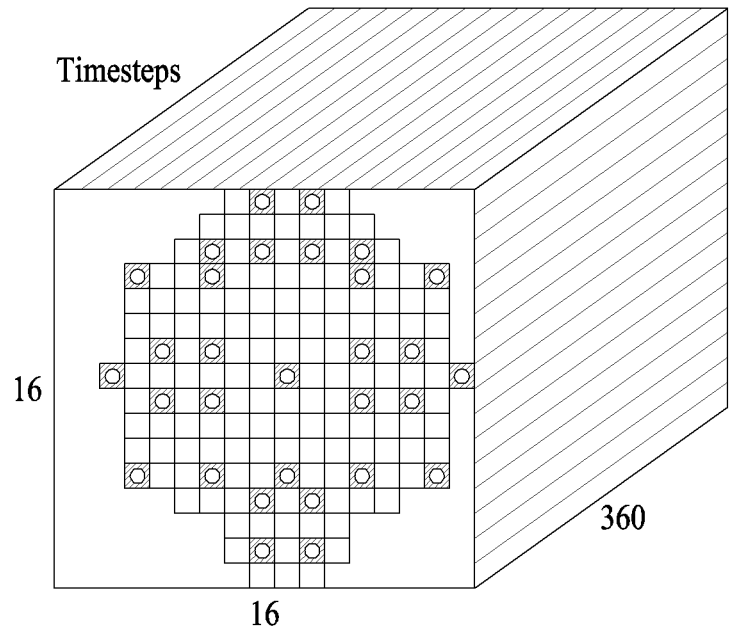
FIG. 10 is a diagram illustrating a 3D EEG tensor and a 3D fNIRS tensor according to an example embodiment.
Figure 10B:
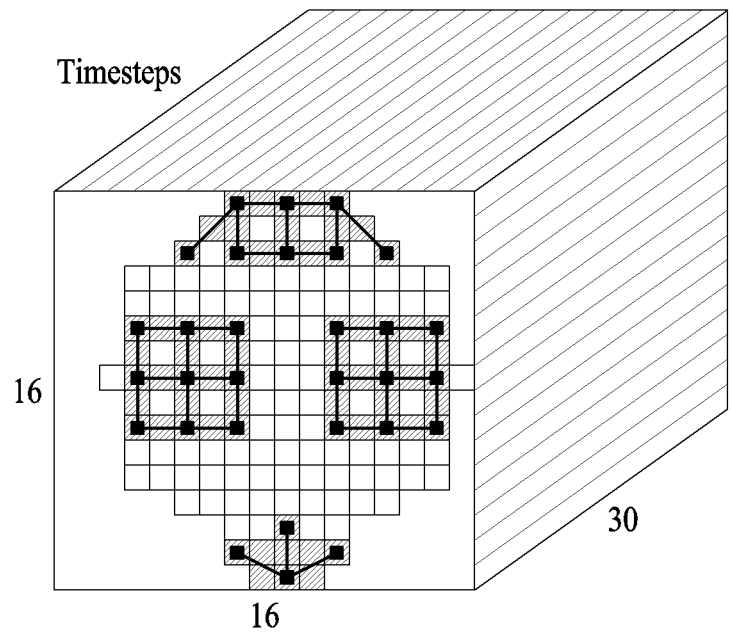

FIG. 10 is a diagram illustrating a 3D EEG tensor and a 3D fNIRS tensor according to an example embodiment. FIG. 10A may be a 3D EEG tensor generated from the EEG signals 110 and 310, and FIG. 10B may be a 3D fNIRS tensor generated from the fNIRS signals 120 and 320.

Spatiotemporal dynamics of the brain may represent a complex cognitive process. For example, theta oscillations (4 to 8 Hz) in the prefrontal cortex may be associated with cognitive workload, alpha oscillations (8 to 12 Hz) in the parietal cortex may indicate visual attention, and beta oscillations (15 to 25 Hz) in the sensorimotor domain may be correlated with mental simulations of behavior.

For example, the training apparatus 300 may convert the 1D EEG signals 110 and 310 to 3D EEG tensors, to include spatiotemporal information in input data (e.g., an MA data set or an MI data set) for training the neural network model 200.

For example, the training apparatus 300 may use azimuthal equidistant projection to obtain a 3D EEG tensor or an image, and project a position of a 3D electrode on the scalp of a measurement target as a 2D image having a size of 16×16 such as FIG. 10A. Data of a point mapped to a 2D image may be filled with time information of a corresponding electrode.

For example, the training apparatus 300 may interpolate empty values between electrodes using cubic spline interpolation. For example, the training apparatus 300 may generate a 3D EEG image of a size of 16×16×360. The 3D EEG image $X^{eeg}$ may include spatial information of a first two dimensions (e.g., 116×16) and time information of a last dimension (e.g., 360).

The fNIRS signals 120 and 320 may be measured using a source emitting near-infrared light and a detector receiving light diffused from brain tissue. To obtain hemodynamic changes due to neural activity, the detected raw fNIRS signals 120 and 320 may have to be converted into changes in HbO and HbR. Since HbO and HbR have different absorption coefficients for near-infrared light of different wavelengths, the changes in HbO and HbR may be calculated as a ratio of an intensity of incident light to an intensity of detection light with respect to light of two different wavelengths.

For example, the training apparatus 300 may calculate a change in concentrations of HbO and HbR in a task period with respect to a time window of a baseline state by using the Beer-Lambert equation. For example, the baseline period may be defined as a time window from −5 s to −2 s of FIG. 9.

The EEG signals 110 and 310 and the fNIRS signals 120 and 320 may have a close spatial correlation due to neurovascular coupling. Accordingly, the training apparatus 300 may convert the 1D fNIRS signal 120 and 320 into a 3D fNIRS tensor in substantially the same manner as the method by which the 3D EEG tensor is generated, to utilize the spatial correlation between the EEG signals 110 and 310 and the fNIRS signals 120 and 320.

Unlike the EEG signals 110 and 310, the fNIRS signals 120 and 320 may be measured by a source and a detector, and as shown in FIG. 10B, a path between the source and the detector may be filled with the same HbO or HbR value.

For example, the training apparatus 300 may interpolate an empty value between the source and the detector using cubic spline interpolation in substantially the same manner as the method by which the EEG signals 110 and 310 are processed. The training apparatus 300 may generate a 3D fNIRS image $X^{fnirs} \in \mathbb{R}^{16 \times 16 \times 30}$ with a size of 16×16×360, and the 3D fNIRS image $X^{fnirs}$ may be spatially aligned with a 3D EEG image $X^{eeg}$.

With reference to FIGS. 8 to 10, an example of the training apparatus 300 for training the neural network model 200 collecting the EEG signals 110 and 310 and/or fNIRS signals 120 and 320 corresponding to the MI task or the MA task, and processing the collected EEG signals 110 and 310 and/or fNIRS signals 120 and 320 to generate data sets (e.g., the MA data set and/or MI data set) for training the neural network model 200 has been described.

For example, the description of the training apparatus 300 collecting and processing the EEG signals 110 and 310 and the fNIRS signals 120 and 320 to generate a 3D EEG tensor and/or a 3D fNIRS tensor may substantially equally apply to an operation of the electronic device 100 for collecting and processing the EEG signals 110 and 310 and the fNIRS signals 120 and 320 to generate a 3D EEG tensor and/or a 3D fNIRS tensor.

For example, the 3D EEG tensor and/or the 3D fNIRS tensor of the MI data set generated by the training apparatus 300 may be labeled as left-hand MI task or right-hand MI task. For example, the 3D EEG tensor and/or the 3D fNIRS tensor of the MA data set generated by the training apparatus 300 may be labeled as baseline state or an MA task.

In an example embodiment, the EEG signals 110 and 310 and the fNIRS signals 120 and 320 of the MI data set or the MA data set may be divided into a 3-second segment using a 1-second sliding window from −2 s to 10 s of FIG. 9 in which the instruction period and the task period are included, and each of the EEG signals 110 and 310 and the fNIRS signals 120 and 320 may be divided into 10 segments (e.g., −2 s-1 s, −1 s-2 s, . . . , 7-10 s). For example, the (t−3) s-ts time window may be defined as a ts time segment.

Figure 11:
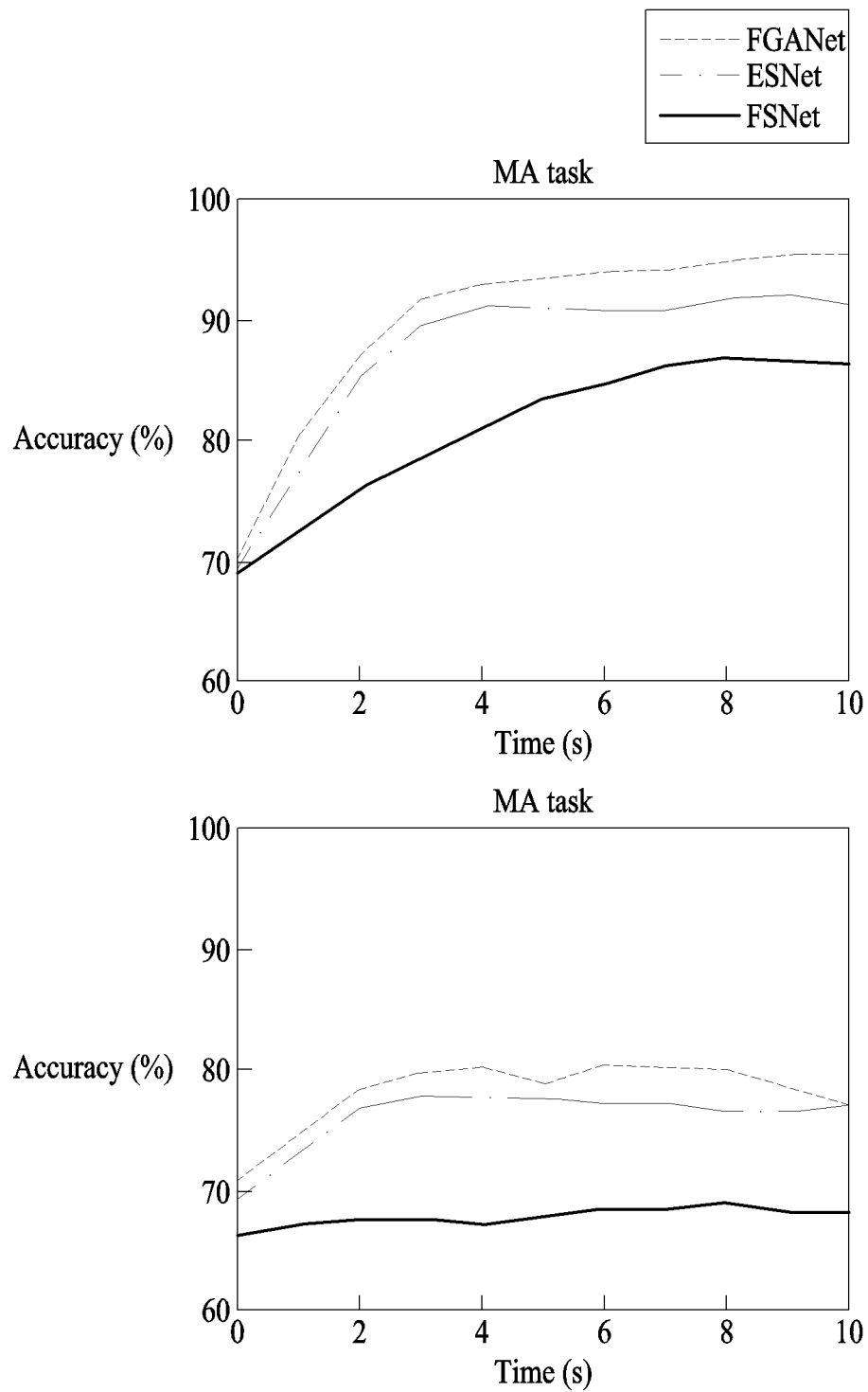
FIGS. 11 and 12 are diagrams illustrating performance of a neural network model according to an example embodiment.
Figure 12:
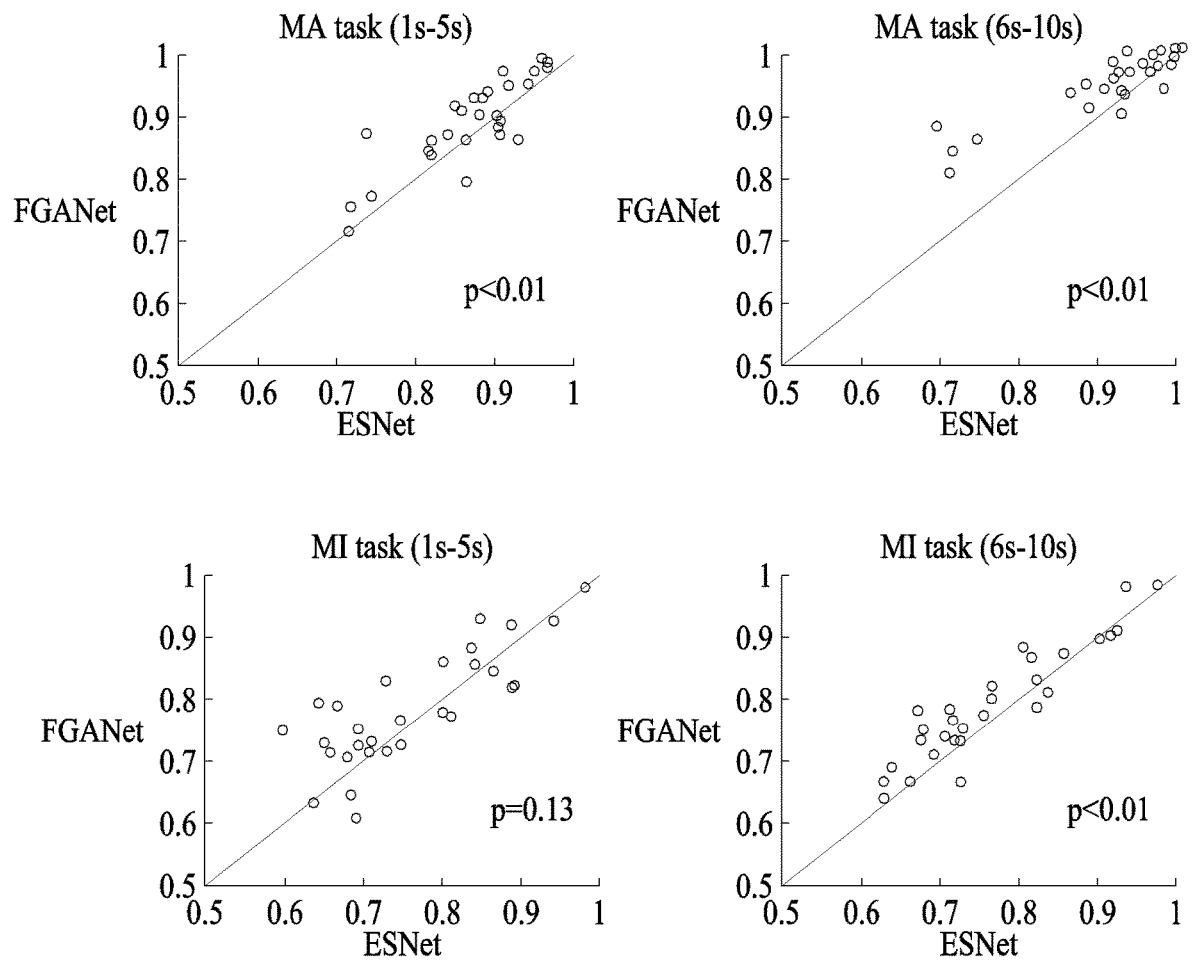

FIGS. 11 and 12 are diagrams illustrating performance of a neural network model 200 according to an example embodiment.

In an example embodiment, the training apparatus 300 may train the neural network model 200 using the training data (e.g., the MA data set or the MI data set) described with reference to FIGS. 8 to 10. For example, the neural network model 200 trained by the training apparatus 300 may measure performance via 5-fold cross validation for each measurement target, and calculate the performance based on an average. A final performance of the trained neural network model 200 may be calculated as an average of the performance measured for all measurement targets. An average accuracy may be calculated as an average of an accuracy of 10 segments.

In an example embodiment, the training apparatus 300 may use an Adam optimizer to update a network parameter of the neural network model 200 at a learning rate of 0.001 for 200 epochs.

For example, the training apparatus 300 may set an initial trainable residual parameter $\gamma_{train}$ to 0. For example, the training apparatus 300 may use a parameter fine tuning process to optimize a network parameter and a regularization parameter. For example, the training apparatus 300 may use 90% of the total number of training data items (e.g., 1740 pieces, 29 subjects×30 trials×2 tasks) for training, and use 10% thereof as verification data.

For example, a kernel and a stride for a temporal dimension of the first convolutional layer (e.g., Conv1, Conv4, and Conv7 of FIG. 4) may be optimized from a kernel and stride set, and the regularization parameter λ may be optimized from a regularization parameter set. For example, the kernel and stride set may be (kernal, stride)∈[(7, 2), (7, 4), (9, 2), (9, 4)], and the regularization parameter set may be [1, 0.1, 0.01, 0.001]. The optimized kernel and stride of the first convolutional layer may be as shown in Table 1 above, and the optimized regularization parameter λ may be set to 0.1.

FIG. 11 shows a classification result of the neural network model 200 for a moving time window. In FIG. 11, a horizontal axis may indicate a right edge (e.g., the t in (t−3) s-ts time window) of the moving time window, and a vertical axis may indicate accuracy. In FIG. 11, it may be confirmed that the neural network model 200 (e.g., FGANet) trained by the training apparatus 300 has a higher performance in processing both MA and MI tasks compared to the neural network model 200 (e.g., ESNet and FSNet) trained by other training methods.

FIG. 12 shows a result of performing a paired t-test to compare the performances of the neural network model 200 trained by the training apparatus 300 and the neural network model 200 (e.g., ESNet) trained by other methods, by dividing the MA task and the MI task into a first half group (1 s-5 s) and a second half group (6 s-10 s).

The neural network model 200 trained by the training apparatus 300 may have a higher performance (p<0.01) compared to the neural network model 200 trained by other methods in the first half and the second half groups of the MA task, and the second half group of the MI task.

Table 3 below shows a result of an ablation study to confirm the performance of the neural network model 200 trained according to various example embodiments. In Table 3 below, "–" may indicate that a corresponding configuration has been removed, and Table 3 may indicate the classification accuracy of the neural network model 200 for the MA task or the MI task, respectively, as a mean and a standard deviation. Referring to Table 3 below, it may be confirmed that the TAP layer improves the average accuracy by about 1% in the MA task.

TABLE 3

| Task | Model | Mean Acc (%) | Max Acc (%) |
|---|---|---|---|
| MA task | FGANet | 91.96 ± 05.82 | 95.46 ± 05.12 |
| | TAP layer | 91.02 ± 06.14 | 94.71 ± 06.09 |
| | residual parameter | 91.32 ± 08.66 | 94.60 ± 10.58 |
| | FGA map regularization | 90.81 ± 05.80 | 93.79 ± 05.27 |
| | weighted prediction | 91.42 ± 06.07 | 94.71 ± 05.31 |
| MI task | FGANet | 78.59 ± 05.82 | 80.23 ± 05.12 |
| | TAP layer | 78.12 ± 08.89 | 79.94 ± 10.88 |
| | residual parameter | 77.93 ± 08.66 | 79.60 ± 10.58 |
| | FGA map regularization | 76.58 ± 08.64 | 78.16 ± 10.03 |
| | weighted prediction | 77.44 ± 08.95 | 79.77 ± 09.22 |

Referring to Table 3, regarding the effect of FGA map regularization on performance, it may be confirmed that performance is lower when FGA map regularization is not performed in both the MI task and the MA task. FGA map regularization may be a correlation coefficient loss $L_{fga}$. This may imply that fusion performance of the EEG signal and the fNIRS signal may be improved by training model parameters to enhance the spatial correlation between the EEG signal and the fNIRS signal.

Referring to Table 3, using a weighted prediction method may improve the performance of the neural network model 200 by alleviating performance degradation due to a delayed hemodynamic response.

Table 4 below shows a comparison of the performance of the neural network model 200 trained according to various example embodiments and the performance of the neural network model trained according to other methods. In Table 4, "†" may denote performance of an implementation model for an existing algorithm, and "*" may denote a model showing a significant difference from the neural network model 200 trained according to various example embodiments. In Table 4, "FGANet" may be the neural network model 200 trained according to various example embodiments.

TABLE 4

| Algorithm | Signal type | MA task | | MI task | |
| --- | --- | --- | --- | --- | --- |
| | | Mean Acc (%) | Max Acc (%) | Mean Acc (%) | Max Acc (%) |
| Ergun et al. [54] | EEG | — | 88.71 | — | — |
| Ergun et al. [55] | fNIRS | — | 84.94 | — | — |
| Ergun et al. [56] | fNIRS | — | — | — | 72.36 |
| Aydin et al. [57] | fNIRS | — | 89.54 | — | 78.27 |
| IDPF [25] | EEG + fNIRS | — | 91.15 | — | 78.56 |
| Shin et al.† [20] | EEG + fNIRS | 75.60* ± 06.69 | 84.29* ± 09.07 | 60.91* ± 09.07 | 63.85* ± 10.83 |
| pth-PF† [33] | EEG + fNIRS | 87.24* ± 06.14 | 91.67* ± 06.09 | 75.90* ± 08.89 | 77.36* ± 10.88 |
| pth-PF† (EEG + fNIRS branch) | EEG + fNIRS | 87.95* ± 05.80 | 92.53* ± 05.27 | 73.10* ± 08.64 | 74.20* ± 10.03 |
| pth-PF† (EEG + fusion branch) | EEG + fNIRS | 87.99* ± 06.67 | 93.05* ± 05.89 | 74.67* ± 08.41 | 76.26* ± 09.88 |
| ESNet | EEG | 89.14* ± 07.73 | 92.07* ± 08.42 | 76.50* ± 09.63 | 77.47* ± 10.71 |
| FSNet | fNIRS | 82.34* ± 08.11 | 86.95* ± 09.19 | 67.80* ± 08.23 | 68.68* ± 09.00 |
| FGANet | EEG + fNIRS | 91.96* ± 05.82 | 95.46* ± 0.512 | 78.59* ± 08.86 | 80.23* ± 09.63 |

Figure 13:
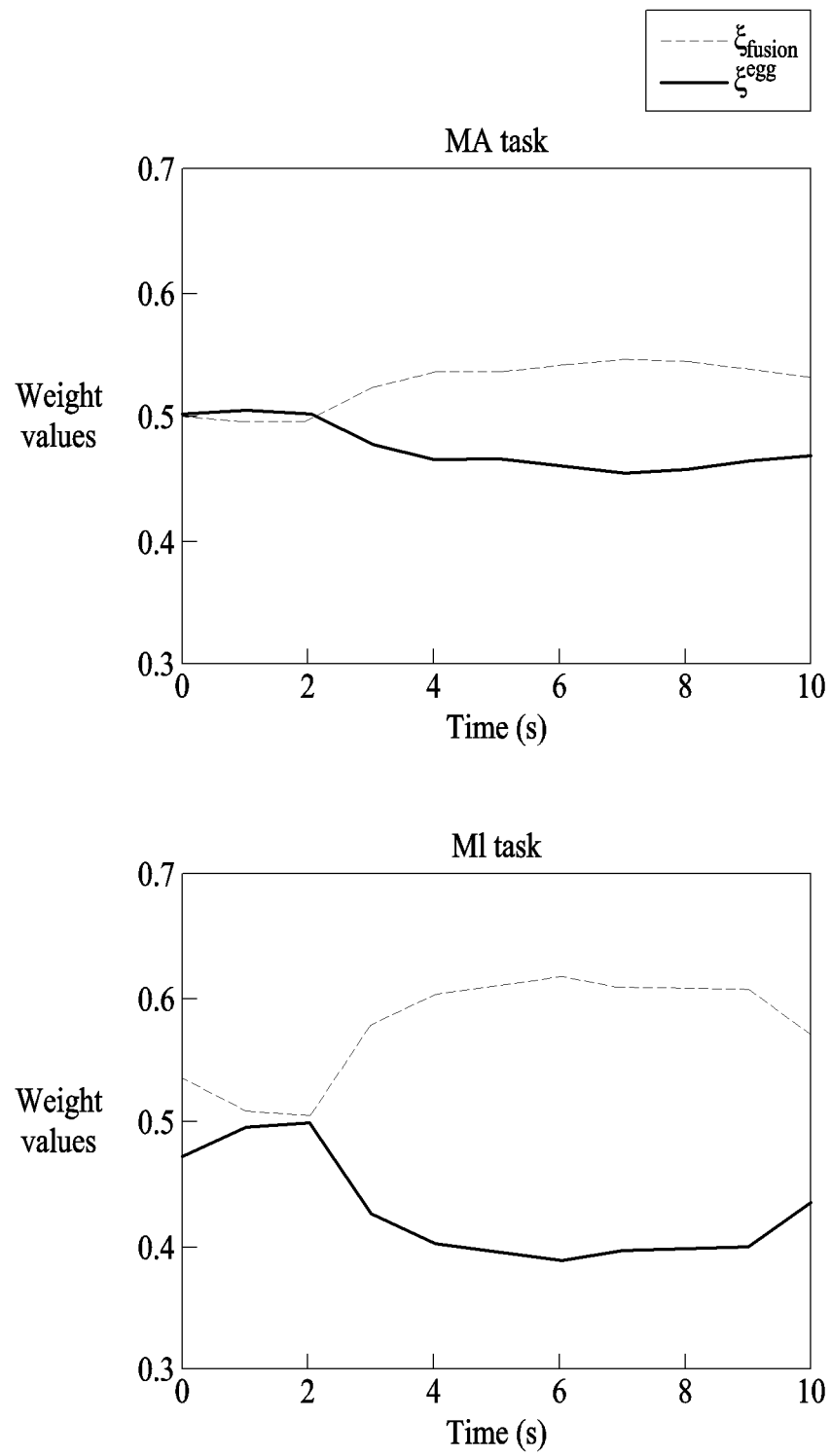
FIG. 13 is a diagram illustrating a change in a prediction weight vector with respect to a moving time window according to an example embodiment.

FIG. 13 is a diagram illustrating a change in a prediction weight vector (e.g., the prediction weight vector of FIG. 4 or Equation 2) with respect to a moving time window according to an example embodiment.

In FIG. 13, it may be confirmed that a weight $\xi^{fusion}$ assigned to a second result increases in both the MA task and the MI task after 2 s from about 0.5 at 0 s. For example, the weight with respect to the second result $\xi^{fusion}$ may be understood to reflect a delay of hemodynamic response of the fNIRS signals 120 and 320.

In an example embodiment, the neural network model 200 may reflect spatial information included in the fNIRS signals 120 and 320 to the EEG signals 110 and 310 by outputting a result based on a first result and a second result, to determine brain activity. In an example embodiment, the neural network model 200 may adaptively adjust at least one of the prediction weights $\xi^{eeg}$ or $\xi^{fusion}$ according to an importance of the fNIRS signals 120 and 320.

Figure 14:
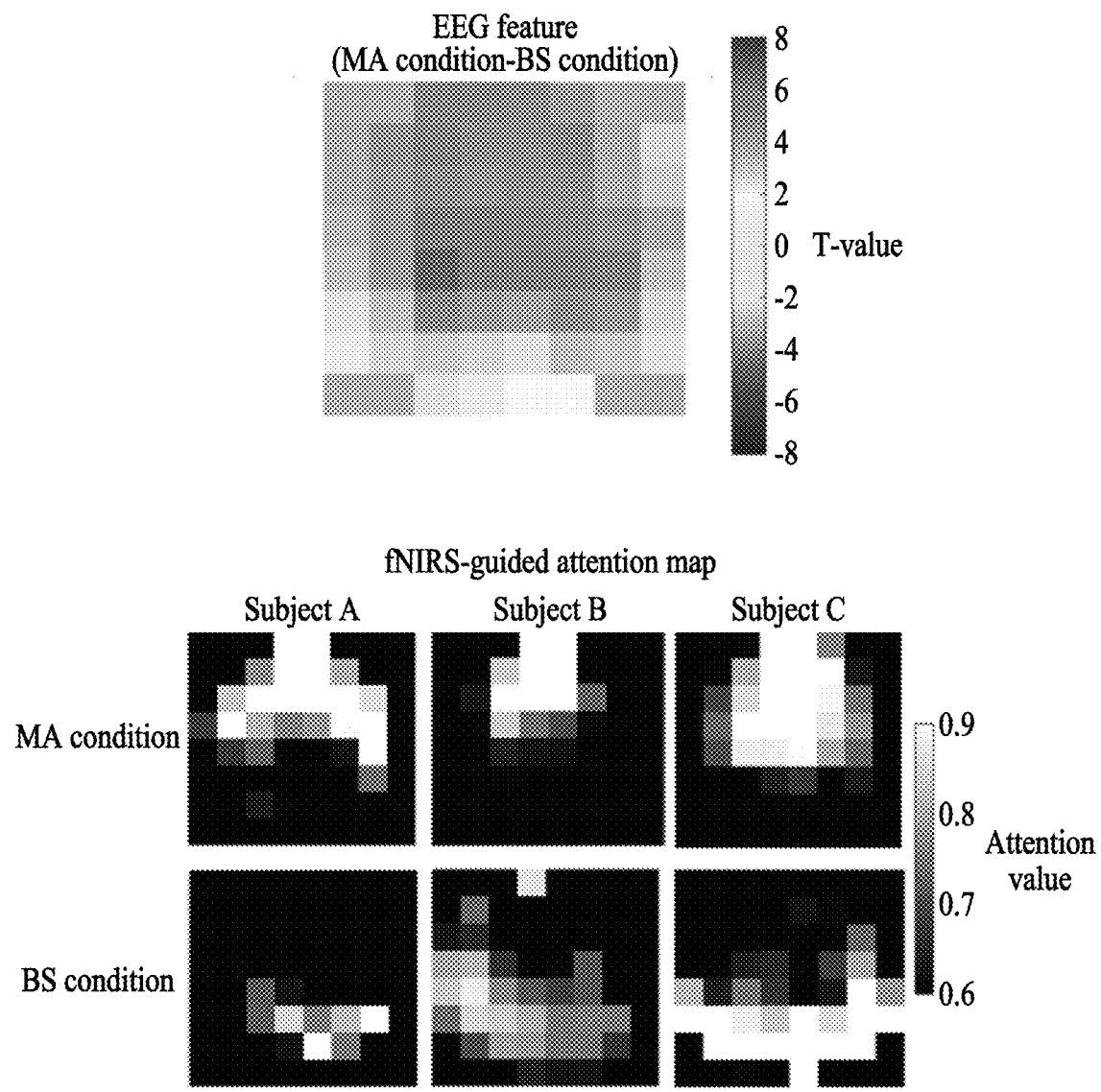
FIG. 14 is a diagram illustrating an EEG feature and an FGA map visualized as a t-value for a mental arithmetic (MA) task according to an example embodiment.
Figure 15:
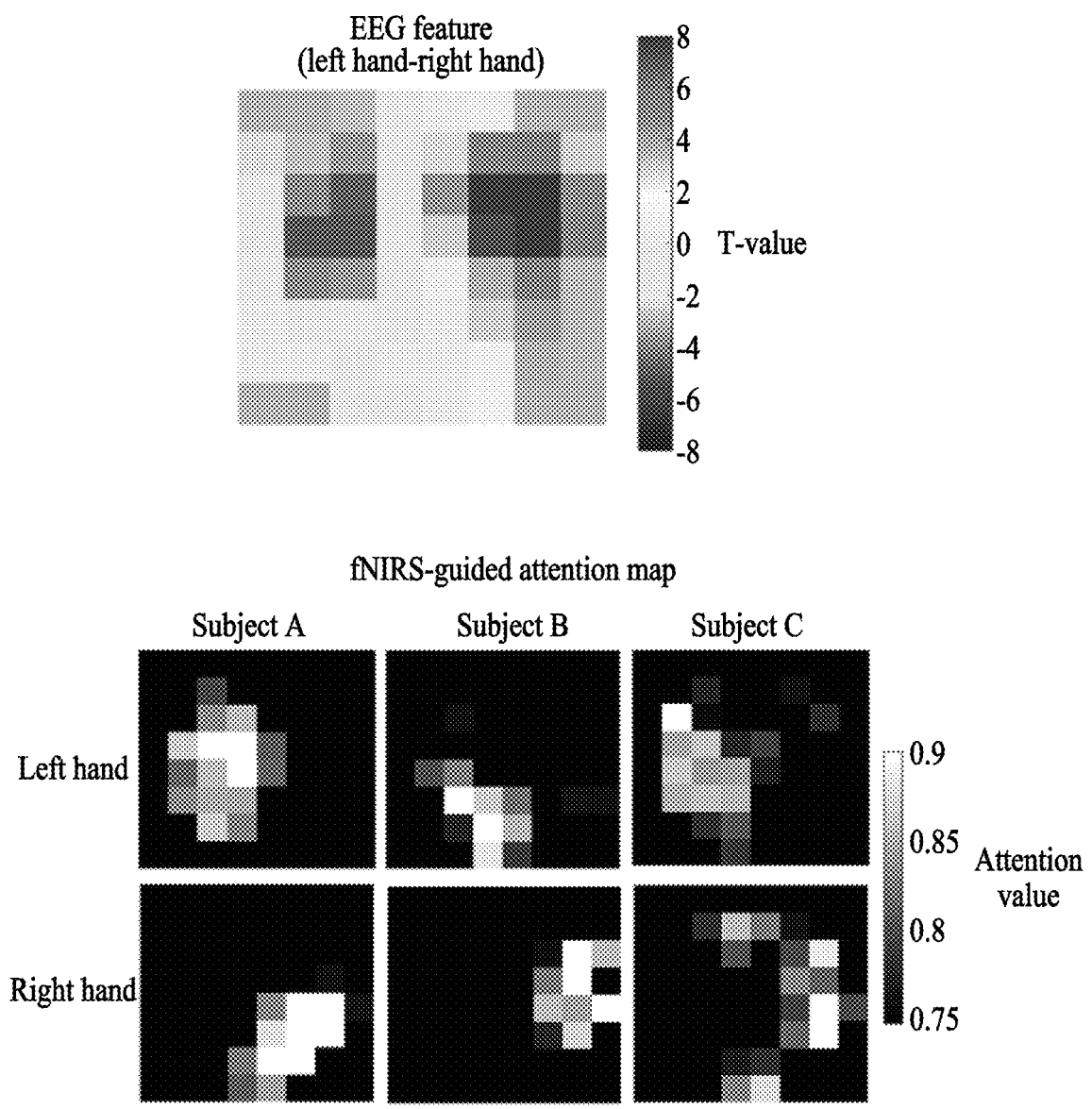
FIG. 15 is a diagram illustrating an EEG feature and an FGA map visualized as a t-value for a motor imagery (MI) task according to an example embodiment.

FIGS. 14 and 15 are diagrams illustrating EEG features and FGA maps visualized as t-values for an MI task and an MA task according to an example embodiment. For example, the EEG features visualized in FIGS. 14 and 15 may represent $\hat{F}^{fusion(1)}$ of FIG. 4 and the FGA maps may represent $\Phi^{(1)}$.

For example, the t-value may be used to find a discriminant region between two classes. Regions with high t-values of EEG features may indicate regions where activation values of class 1 (e.g., MA task or left-hand MI task) are high, and activation values of class 2 (e.g., baseline state or right-hand MI task) are high, and regions with low t-values may indicate the opposite.

For example, a higher attention value in the FGA map may indicate an important region for brain decoding extracted from the fNIRS signals 120 and 320.

It may be confirmed that the EEG feature of the MA task (MA condition) in FIG. 14 is high in all feature regions of the baseline state (BS condition), which is consistent with a result of theta (4-8 Hz) power increasing as workload increases.

In FIG. 14, it may be seen that the t-value in an upper region of the EEG feature is higher than in a lower region of the EEG feature, and the same trend may be confirmed in the FGA map. Referring to FIG. 14, the FGA map may appropriately highlight identifiable regions of EEG features.

It may be seen that the t-value of the EEG feature in FIG. 15 is a positive number in a right region and a negative number in a left region. Referring to the visualized EEG feature of FIG. 15, when a measurement target imagines moving the left hand, it may indicate that an EEG feature value of the left region is higher, and when the measurement target imagines moving the right hand, it may indicate that an EEG feature value of the right region is higher. It may be confirmed that the results shown in FIG. 15 are similar to reported results from other studies showing that due to an inhibition process, the motion images of the left hand have a positive correlation with the left middle lobe, while the motion images of the right hand have a positive correlation with the right middle lobe.

In the FGA map of FIG. 15, it may be confirmed that the left region is activated when the left-hand MI task is performed, and the right region is activated when the right-hand MI task is performed. Accordingly, it may be confirmed that the FGA map may extract an important region for decoding the EEG signals 110 and 310 from the left-hand MI task or the right-hand MI task.

Figure 16:
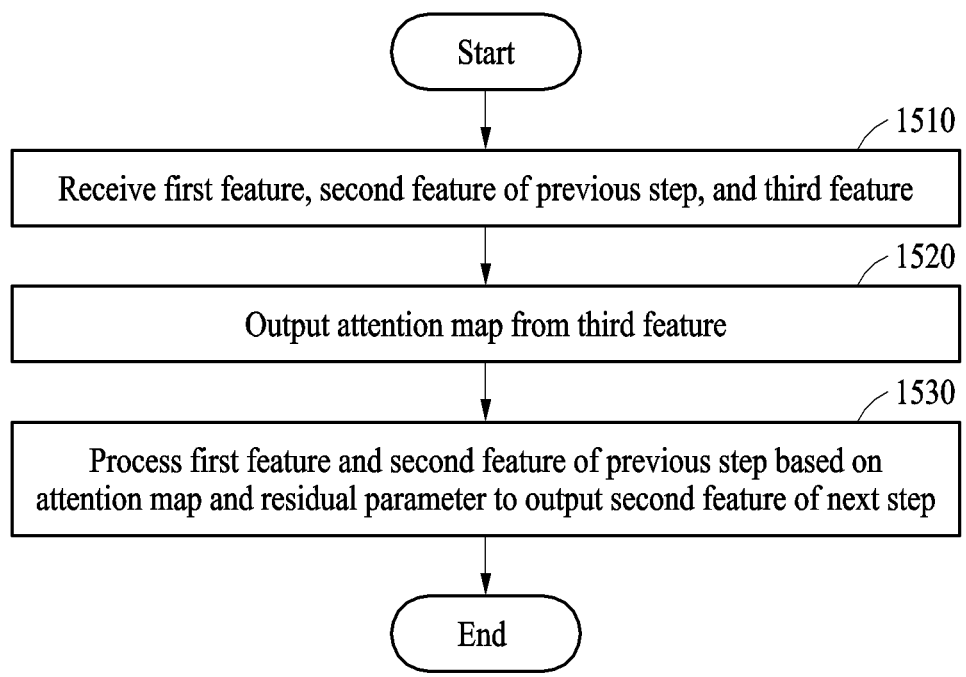
FIG. 16 is a diagram illustrating a data processing method according to an example embodiment.

FIG. 16 is a diagram illustrating a data processing method according to an example embodiment.

The data processing method illustrated in FIG. 16 may be performed by a data processing apparatus. For example, the data processing apparatus may include a layer that is the same as the FGA layer illustrated in FIG. 6. For example, the data processing apparatus may include a 3D convolutional layer, a TAP layer, and the like shown in FIG. 6.

Referring to FIG. 16, the data processing apparatus according to various example embodiments may receive a first feature, a second feature of a previous step, and a third feature in operation 1510. In an example embodiment, the first feature, the second feature of the previous step, and/or the third feature may be a 3D image or a 3D tensor. For example, the first feature, the second feature of the previous step, and/or the third feature may have dimensions such as height, width, time, and channel.

In an example embodiment, the data processing apparatus may output an attention map from the third feature in operation 1520. For example, the data processing apparatus may compress a channel of the third feature by using a 3D convolutional layer. For example, the data processing apparatus may process the third feature in which the channel is compressed according to a TAP layer and a sigmoid function to output the attention map.

For example, the data processing apparatus may process a third feature of a size of H×x×W×T'@C' using a 3D convolutional layer to output a feature of a size of H×W×T'@1. For example, the data processing apparatus may process the H×W×T'@1 size feature according to the TAP layer and the sigmoid function to output an H×W×1@1 size attention map. For example, the TAP layer may be the TAP layer shown in FIG. 5.

For example, the data processing apparatus may assign a large weight to a predetermined dimension (e.g., a time dimension of the third feature) of the third feature using the TAP layer. An attention map output by the data processing device may be a weight matrix for a predetermined dimension (e.g., a spatial dimension (H×W) of the third feature). For example, the data processing apparatus may apply an attention to the second feature using the attention map.

For example, in operation 1530, the data processing apparatus may process the first feature and the second feature of the previous step based on the attention map and a residual parameter to output a second feature of a next step. For example, as shown in Equation 16 below, the data processing apparatus may output a second feature $\hat{F}_{f,w,t,c}^2$ of a next step, by processing a first feature $F_{h,w,t,c}^1$ and a second feature $F_{h,w,t,c}^2$ of a previous step based on a residual parameter $\gamma$· and an attention map $\Phi_{h,w,1,1}$·.

$$\hat{F}_{h,w,t,c}^2 = \gamma F_{h,w,t,c}^1 + (1-\gamma) F_{h,w,t,c}^2 + \Phi_{h,w,1,1} F_{h,w,t,c}^2 \quad \text{[Equation 16]}$$

For example, in the data processing method shown in FIG. 16, each signal may have a correlation, such as when an fNIRS signal and an EEG signal simultaneously measure brain activity, but when each signal has a different correlation in a time dimension, a feature may be extracted by fusing each signal.

The method according to example embodiments may be written in a computer-executable program and may be implemented as various recording media such as magnetic storage media, optical reading media, or digital storage media.

Various techniques described herein may be implemented in digital electronic circuitry, computer hardware, firmware, software, or combinations thereof. The implementations may be achieved as a computer program product, i.e., a computer program tangibly embodied in an information carrier, e.g., in a machine-readable storage device (for example, a computer-readable medium) or in a propagated signal, for processing by, or to control an operation of, a data processing apparatus, e.g., a programmable processor, a computer, or multiple computers. A computer program, such as the computer program(s) described above, may be written in any form of a programming language, including compiled or interpreted languages, and may be deployed in any form, including as a stand-alone program or as a module, a component, a subroutine, or other units suitable for use in a computing environment. A computer program may be deployed to be processed on one computer or multiple computers at one site or distributed across multiple sites and interconnected by a communication network.

Processors suitable for processing of a computer program include, by way of example, both general and special purpose microprocessors, and any one or more processors of any kind of digital computer. Generally, a processor will receive instructions and data from a read-only memory or a random-access memory, or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Examples of information carriers suitable for embodying computer program instructions and data include semiconductor memory devices, e.g., magnetic media such as hard disks, floppy disks, and magnetic tape, optical media such as compact disk read only memory (CD-ROM) or digital video disks (DVDs), magneto-optical media such as floptical disks, read-only memory (ROM), random-access memory (RAM), flash memory, erasable programmable ROM (EPROM), or electrically erasable programmable ROM (EEPROM). The processor and the memory may be supplemented by, or incorporated in special purpose logic circuitry.

In addition, non-transitory computer-readable media may be any available media that may be accessed by a computer and may include both computer storage media and transmission media.

Although the present specification includes details of a plurality of specific example embodiments, the details should not be construed as limiting any invention or a scope that can be claimed, but rather should be construed as being descriptions of features that may be peculiar to specific example embodiments of specific inventions. Specific features described in the present specification in the context of individual example embodiments may be combined and implemented in a single example embodiment. On the contrary, various features described in the context of a single example embodiment may be implemented in a plurality of example embodiments individually or in any appropriate sub-combination. Furthermore, although features may operate in a specific combination and may be initially depicted as being claimed, one or more features of a claimed combination may be excluded from the combination in some cases, and the claimed combination may be changed into a sub-combination or a modification of the sub-combination.

Likewise, although operations are depicted in a specific order in the drawings, it should not be understood that the operations must be performed in the depicted specific order or sequential order or all the shown operations must be performed in order to obtain a preferred result. In specific cases, multitasking and parallel processing may be advantageous. In addition, it should not be understood that the separation of various device components of the aforementioned example embodiments is required for all the example embodiments, and it should be understood that the aforementioned program components and apparatuses may be integrated into a single software product or packaged into multiple software products.

The example embodiments disclosed in the present specification and the drawings are intended merely to present specific examples in order to promote understanding of the present disclosure, but are not intended to limit the scope of the present disclosure. It will be apparent to those skilled in the art that various modifications based on the technical spirit of the present disclosure, as well as the disclosed example embodiments, can be made.

EXPLANATION OF REFERENCE NUMERALS

100: electronic device
110, 310: EEG signal 120, 320: fNIRS signal
130, 330: result
200: neural network model
210: EEG branch
215: first result
220: fusion branch
225: second result
230: fNIRS branch
235: third result
340: loss.

What is claimed is:

1. An electronic device, comprising:
a processor; and
a memory operatively connected to the processor and comprising instructions executable by the processor,
wherein, when the instructions are executed, the processor is configured to:
collect an EEG signal measuring brain activity and an fNIRS signal measuring the brain activity; and
output a result of determining a type of the brain activity from a trained neural network model using the EEG signal and the fNIRS signal, and
the neural network model is trained to:
extract an EEG feature from the EEG signal using an EEG branch comprising a plurality of sequentially connected convolutional layers;
extract an fNIRS feature from the fNIRS signal using an fNIRS branch comprising a plurality of sequentially connected convolutional layers;
extract a fusion feature based on the EEG signal and the fNIRS signal using a fusion branch comprising a plurality of sequentially connected convolutional layers and an fNIRS-guided attention (FGA) layer; and
output the result of determining the type of the brain activity based on the EEG feature and the fusion feature.

2. The electronic device of claim 1, wherein the FGA layer is configured to output a fusion feature of a next step using the input EEG feature, a fusion feature of a previous step, and the fNIRS feature, and
the fusion feature of the previous step is output from a convolutional layer of a front-end of the FGA layer, and
the fusion feature of the next step is input to a convolutional layer or a temporal attention pooling (TAP) layer of a back-end of the FGA layer.

3. The electronic device of claim 2, wherein the FGA layer is configured to:
output an FGA map from the fNIRS feature by applying a weight to a time segment related to the brain activity using the TAP layer comprised in the FGA layer; and
output the fusion feature of the next step by processing the EEG feature and the fusion feature of the previous step according to the FGA map and a residual parameter.

4. The electronic device of claim 2, wherein the TAP layer is configured to compress a feature having input height, width, time, and channel dimensions on a time axis of the feature.

5. The electronic device of claim 1, wherein the neural network model is configured to:
output a first result based on the EEG feature;
output a second result based on the fusion feature; and
output the result by applying a weight assigned to each of the first result and the second result.

6. A method of determining brain activity, the method comprising:
collecting an EEG signal measuring brain activity and an fNIRS signal measuring the brain activity; and
outputting a result of determining a type of the brain activity from a trained neural network model using the EEG signal and the fNIRS signal, and
wherein the neural network model is trained to:
extract an EEG feature from the EEG signal using an EEG branch comprising a plurality of sequentially connected convolutional layers;
extract an fNIRS feature from the fNIRS signal using an fNIRS branch comprising a plurality of sequentially connected convolutional layers;
extract a fusion feature based on the EEG signal and the fNIRS signal using a fusion branch comprising a plurality of sequentially connected convolutional layers and an FGA layer; and
output the result of determining the type of the brain activity based on the EEG feature and the fusion feature.

7. The method of claim 6, wherein the FGA layer is configured to output a fusion feature of a next step using the input EEG feature, a fusion feature of a previous step, and the fNIRS feature, and
the fusion feature of the previous step is output from a convolutional layer of a front-end of the FGA layer, and
the fusion feature of the next step is input to a convolutional layer or a TAP layer of a back-end of the FGA layer.

8. The method of claim 7, wherein the FGA layer is configured to:
output an FGA map from the fNIRS feature by applying a weight to a time segment related to the brain activity using the TAP layer comprised in the FGA layer; and
output the fusion feature of the next step by processing the EEG feature and the fusion feature of the previous step according to the FGA map and a residual parameter.

9. A training method of a neural network model, the training method comprising:
collecting an EEG signal measuring brain activity and an fNIRS signal measuring the brain activity of a motor imagery (MI) data set or a mental arithmetic (MA) data set;
extracting an EEG feature from the EEG signal using an EEG branch comprising a plurality of sequentially connected convolutional layers;
extracting an fNIRS feature from the fNIRS signal using an fNIRS branch comprising a plurality of sequentially connected convolutional layers;
extracting a fusion feature based on the EEG signal and the fNIRS signal using a fusion branch comprising a plurality of sequentially connected convolutional layers and an FGA layer;
outputting a result of determining a type of the brain activity based on the EEG feature and the fusion feature;
calculating a loss based on the result and a labeling of the EEG signal and the fNIRS signal; and
training a neural network model using the loss.

10. The training method of claim 9, wherein the extracting of the fusion feature comprises outputting a fusion feature of a next step by inputting the EEG feature, a fusion feature of a previous step, and the fNIRS feature, and
the fusion feature of the previous step is output from a convolutional layer of a front-end of the FGA layer, and
the fusion feature of the next step is input to a convolutional layer or a TAP layer of a back-end of the FGA layer.

11. The training method of claim 10, wherein the FGA layer is configured to:

output an FGA map from the fNIRS feature by applying a weight to a time segment related to the brain activity using the TAP layer comprised in the FGA layer; and output the fusion feature of the next step by processing the EEG feature and the fusion feature of the previous step according to the FGA map and a residual parameter.

12. The training method of claim 10, wherein the TAP layer is configured to compress a feature having input height, width, time, and channel dimensions on a time axis of the feature.

13. The training method of claim 9, wherein the outputting of the result of the determining comprises:

outputting a first determination result based on the EEG feature;

outputting a second determination result based on the fusion feature; and applying a weight assigned to each of the first determination result and the second determination result.

14. The training method of claim 9, wherein the calculating of the loss comprises:

calculating a classification loss based on the result and the labeling;

calculating an fNIRS classification loss (cross entropy loss) of the fNIRS branch based on the fNIRS feature; and calculating a correlation coefficient loss of the EEG signal and the fNIRS signal.

* * * * *